(12) United States Patent
Hoffman et al.

(10) Patent No.: US 11,380,435 B2
(45) Date of Patent: Jul. 5, 2022

(54) AUTOMATED ASSISTANCE PROGRAM QUALIFICATION AND ENROLLMENT

(71) Applicant: Experian Health, Inc., Franklin, TN (US)

(72) Inventors: Paul Joseph Hoffman, Mill Valley, CA (US); Sean M. Porter, Plymouth, MN (US); Kevin Otto Horvath, Bloomingdale, IL (US); Elizabeth Donato Serie, Maple Grove, MN (US)

(73) Assignee: EXPERIAN HEALTH, INC., Franklin, TN (US)

( * ) Notice: Subject to any disclaimer, the term of this patent is extended or adjusted under 35 U.S.C. 154(b) by 500 days.

(21) Appl. No.: 16/374,453

(22) Filed: Apr. 3, 2019

(65) Prior Publication Data

US 2019/0304599 A1   Oct. 3, 2019

Related U.S. Application Data

(60) Provisional application No. 62/652,139, filed on Apr. 3, 2018.

(51) Int. Cl.
*G16H 40/20* (2018.01)
*G16H 10/20* (2018.01)

(52) U.S. Cl.
CPC .......... *G16H 40/20* (2018.01); *G16H 10/20* (2018.01)

(58) Field of Classification Search
CPC ........ G16H 10/20; G16H 40/20; G06F 19/30; G06F 19/32; G06F 19/34; G06Q 50/22; G06Q 50/24

USPC ......................................................... 705/2-3
See application file for complete search history.

(56) References Cited

U.S. PATENT DOCUMENTS

| | | | | |
|---|---|---|---|---|
| 2002/0062249 A1* | 5/2002 | Iannacci | ............... | G06Q 30/06 705/14.1 |
| 2006/0020360 A1* | 1/2006 | Wu | ........................ | G06Q 10/10 700/104 |
| 2008/0300893 A1* | 12/2008 | Mendoza | ............... | G06Q 10/10 705/1.1 |
| 2010/0318372 A1* | 12/2010 | Band | ...................... | G06Q 30/02 715/825 |
| 2012/0130746 A1* | 5/2012 | Baker | .................... | G16H 40/67 705/3 |

(Continued)

*Primary Examiner* — Michael Tomaszewski
(74) *Attorney, Agent, or Firm* — Knobbe, Martens, Olson & Bear, LLP

(57) ABSTRACT

Automated assistance program qualification and enrollment are provided. An assistance program qualification and enrollment (APQE) system determines whether a user qualifies for an assistance program that offers assistance with an ongoing transaction record with a service provider. The APQE system generates a set of questions based on qualification data (used to make a qualification determination) that are not included in collected user data and financial data about the user. The user's qualification is based on an evaluation of the user data, financial data, and user-provided responses to the questions. If the user qualifies for the assistance program, an option is provided to the user to enroll in the assistance program. If additional information is needed to complete an enrollment process for the assistance program, an interface is provided that enables the user to provide the data for completing the process.

20 Claims, 10 Drawing Sheets

(56) References Cited

U.S. PATENT DOCUMENTS

| | | | |
|---|---|---|---|
| 2013/0110704 A1* | 5/2013 | Padron | G06Q 40/025 |
| | | | 705/38 |
| 2014/0149303 A1* | 5/2014 | Band | G06Q 10/1057 |
| | | | 705/322 |
| 2015/0193749 A1* | 7/2015 | Ivanoff | G16H 50/20 |
| | | | 705/40 |
| 2016/0086222 A1* | 3/2016 | Kurapati | G06Q 40/08 |
| | | | 705/14.53 |
| 2019/0095991 A1* | 3/2019 | Swaminathan | G06Q 50/167 |

* cited by examiner 400    120c

| Application | Review & Submit | Pending | Determination |

Back To Beginning

Person Responsible for Payment                                    424a-n    425a-n

| Last Name | First Name | Middle Initial | Address |
| Watkins | Lisa | | 1234 Main Street |
| City | State | Zip | Telephone |
| Peoria | IL | 61554 | 912-555-9898 |
| Birthday | Age | Soc. Sec. No | Marital Status |
| | | | |
| Employer Last Name | Employer First Name | Employer Middle Initial | Employer Address |
| | | | |
| Employer City | Employer State | Employer Zip | Employer Telephone |
| Pekin | IL | 61554 | |

426

Upload Documents

Drop files here or click to upload.

Previously Uploaded Documents
   xyz.jpg
   Signature_20180129_11026_185.jpg

428

Signature Required

FIG. 4C

AUTOMATED ASSISTANCE PROGRAM QUALIFICATION AND ENROLLMENT

CROSS REFERENCE TO RELATED APPLICATIONS

This application claims the benefit of U.S. Provisional Application No. 62/652,139, having the title of "Automated User Assistance Engine" and the filing date of Apr. 3, 2018, which is incorporated herein by reference in its entirety.

BACKGROUND

Due to a variety of reasons, such as the rising cost of healthcare services and higher deductibles that consumers who utilize healthcare services are facing, healthcare service providers are experiencing an increasing number of consumers who are unable to pay for the healthcare services provided to them. While healthcare service providers oftentimes provide charity care and financial assistance through various financial assistance and charity care programs (under certain guidelines within a predefined policy), the burden to request and apply for such programs is placed on the consumer. Oftentimes, consumers may be unaware that such assistance programs exist, or may be embarrassed to inquire about what financial assistance options may be available. Further, financial assistance and charity care application processes can be tedious and time-consuming. For example, to see whether he/she qualifies for financial assistance or charity care, a consumer may be required to complete one or more forms, gather various supporting documents, submit the form(s) and supporting documentation, provide a manual signature, and then wait (e.g., 30 days) on a review process. The submitted form and supporting documents may then be reviewed by an administrator. During the review process, the administrator may ask for additional documents, and finally, a decision may be made based on the review of the documents.

As can be appreciated, this process involves various manual steps, and is oftentimes confusing, tedious, and time consuming for both consumers and administrators. Additionally or alternatively, the forms and/or the supporting documents are likely to include sensitive information, such as personal identifying information and identifiers, medical information, financial information, and the like. For example, a healthcare service provider may request consumers to transmit one or more of: income tax returns for one or more years, proof of income, such as pay stubs from the past n pay periods, a W-2 withholding statement, social security checks, receipts or deposits, bank statements (e.g., checking and savings), or other documentation that may serve as proof of financial assistance/charity care eligibility. Transmissions of such sensitive data introduce security risks. Further, consumers are transmitting these documents before the consumers are even certain that they qualify for financial assistance or charity care. Thus, these documents are being gathered and transmitted unnecessarily for some consumers, which is an inefficient consumption of computing resources (e.g., processing and storage).

As can be appreciated, current financial assistance and charity care application processes not only result in increased security risks and wasted computing resources, but also increase the likelihood of non-payment of services and the consumption of additional workforce and computing resources allocated to collections for consumers who may need and qualify for financial assistance to pay for healthcare services, but who may not be enrolled in such programs because of unawareness, confusion, or difficulties associated with applying for assistance.

SUMMARY

This summary is provided to introduce a selection of concepts in a simplified form that are further described below in the Detailed Description section. This summary is not intended to identify key features or essential features of the claimed subject matter, nor is it intended as an aid in determining the scope of the claimed subject matter.

Aspects of the disclosure provide automated assistance program qualification and enrollment. An assistance program qualification and enrollment (APQE) system determines whether a user qualifies for an assistance program that offers assistance with an ongoing transaction record with a service provider. The APQE system generates a set of questions based on qualification data (used to make a qualification determination) that are not included in collected user data and financial data about the user. The user's qualification is based on an evaluation of the user data, financial data, and user-provided responses to the questions. If the user qualifies for the assistance program, an option is provided to the user to enroll in the assistance program. If additional information is needed to complete an enrollment process for the assistance program, an interface is provided that enables the user to provide the data for completing the process.

Examples are implemented as a computer process, a computing system, or as an article of manufacture such as a device, computer program product, or computer readable media. According to an aspect, the computer program product is a computer storage media readable by a computer system and encoding a computer program of instructions for executing a computer process.

The details of one or more aspects are set forth in the accompanying drawings and description below. Other features and advantages will be apparent from a reading of the following detailed description and a review of the associated drawings. It is to be understood that the following detailed description is explanatory only and is not restrictive of the claims.

BRIEF DESCRIPTION OF THE DRAWINGS

Further features, aspects, and advantages of the invention represented by the examples described in the present disclosure will become better understood by reference to the following detailed description, appended claims, and accompanying Figures, wherein elements are not to scale so as to more clearly show the details, wherein like reference numbers indicate like elements throughout the several views, and wherein:

FIGS. 4C and 4D are illustrations of an example user interface including a set of additional user-specific questions for obtaining user input data and a document upload interface for obtaining documents needed to enroll the user in an assistance program.

DETAILED DESCRIPTION

Figure 1A:
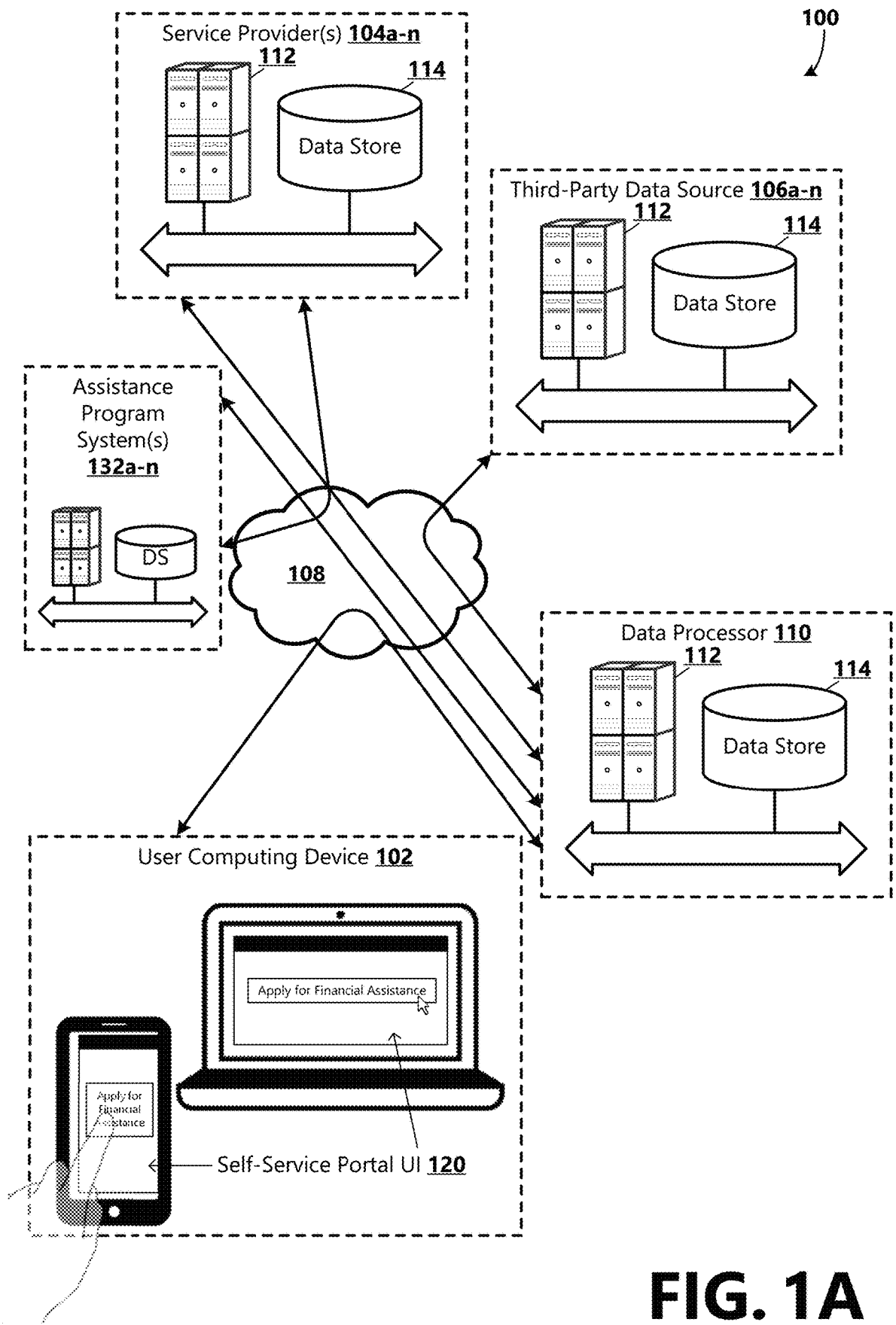
FIG. 1A is a block diagram illustrating an example operating environment in which an automated assistance program qualification and enrollment system may be implemented.

The following detailed description refers to the accompanying drawings. Wherever possible, the same reference numbers are used in the drawings and the following description to refer to the same or similar elements. While aspects of the present disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the present disclosure, but instead, the proper scope of the present disclosure is defined by the appended claims. Examples may take the form of a hardware implementation, or an entirely software implementation, or an implementation combining software and hardware aspects. The following detailed description is, therefore, not to be taken in a limiting sense.

The present disclosure provides a system, method, and computer readable storage device including computer readable instructions, which when executed by a processing unit, provide automated assistance program qualification and enrollment. FIG. 1A is a block diagram illustrating an example operating environment 100 in which automated assistance program qualification and enrollment can be performed. Systems within the example operating environment 100 exchange data and perform analytics to determine whether a user qualifies for one or more financial assistance or charity care programs. A user's qualification for a financial assistance or charity care program is determined based on a profile of the user and user-provided answers to a reduced set of qualification questions that are customized to the user. Aspects of the present disclosure further provide instant (e.g., real-time or near real-time) approval and automatic enrollment for users meeting qualifications for an assistance program. Aspects improve data security and reduce the consumption of computing resources by eliminating transmissions of sensitive data prior to determining a user's qualification based on the user's profile and user responses to the customized qualification questions. If an assistance program policy requires supporting documentation, aspects further enable the user to upload the documentation and to provide a signature from a user computing device. Enabling the various systems and computing devices to exchange data provides access to data related to a user that might not otherwise be available. This data exchange further enables the user to discover and access assistance programs of which the user may otherwise not be aware, which can minimize or at least lower the probability of the user's reneging on his/her obligations as opposed to a system that requires users to search for and manually apply for various financial assistance or charity care programs.

As used herein, the term "assistance program" refers to a program that provides financial assistance or charity care to users who may not have the ability to pay all or part of their financial responsibility to a service provider for provided services; the term "charity care" refers to free care; and the term "financial assistance" refers to discounted care. Such programs can be offered by service providers or by other organizations, such as private companies, charitable organizations, government agencies, and the like, and are defined by particular charity care and financial assistance program policies. Although examples are given herein primarily involving healthcare providers and patients, it will be recognized that the present disclosure is applicable to several fields where persons seeking services are faced with high costs, and the providers are faced with the difficulty of recouping the costs of providing services. Improvements to the efficiency and security of assistance program application and enrollment systems not only improve the systems themselves, but reduce the financial risks to providers in providing services and improve patient access to healthcare, client access to legal services, and student access to educational services, etc.

With reference to FIG. 1A, the example operating environment 100 includes a user computing device 102, one or more service provider systems 104a-n (generally, 104), a data processor system 110, one or more third-party data source systems 106a-n (generally, 106), and optionally one or more third-party assistance program systems 132a-n. Each of the systems 104, 106, 110, 132 include one or more computing devices 112, include one or more data storage devices 114, and are in communication with a network 108 or a combination of networks for exchanging data and coordinating operations to determine a user's qualification for an assistance program and to automatically enroll users who are determined to qualify. The one or more computing devices 112,102 are illustrative of a wide variety of computing devices, the hardware of which is discussed in greater detail in regard to FIG. 5.

The user computing device 102 can be one of various types of computing devices. Non-limiting examples of user computing devices 102 include mobile devices, laptop computers, desktop computers, wearable computing devices, and other computing devices suitable to access a self-service portal system, which provides a user interface 120 through which a user can view ongoing transactions, view and provide answers to a reduced set of customized qualification questions for determining the user's eligibility for an assistance program for covering all or a portion of the ongoing transactions, receive an assistance program qualification/ eligibility response, and, if required, upload and transmit supporting documentation and provide a digital signature to the data processor system 110. For example, the user computing device 102 is configured to communicate with the data processor system 110 via the network 108. The user can be the consumer receiving services from a service provider, a parent or guardian of the consumer, or any other person or entity responsible for the consumer's obligations regarding services rendered. The terms "user" and "consumer" may be used interchangeably herein. The network 108 can be any type of public or private data network for communicating data between computer systems at different entities and at different geographic locations. The Internet is an example of one possible network 108.

The service provider system 104 is configured to generate and store ongoing transaction records relating to consumers. Each ongoing transaction record relates to an encounter with a user and includes information related to a service or services provided to that user. For example, an ongoing transaction record includes obligation information for an encounter (e.g., a bill, follow-up visits, upcoming additional services). Because each service provider generates an ongoing transaction record for a user encounter, there may be multiple ongoing transaction records for each user visit to a provider. For example, a user may be treated in a hospital and the visit may result in ongoing transaction records from the hospital, the treating physician, and the lab.

According to aspects, a variety of assistance programs may be available to cover all or a portion of a user's ongoing transactions with a service provider. These assistance programs can include assistance programs provided by the service provider and/or assistance programs provided by third-party organizations, such as private companies, charitable organizations, and government agencies. Financial assistance provided by an assistance program is offered to users who qualify for the program. Guidelines and criteria for qualification for an assistance program may be defined by service provider policies and assistance program rules. For example, the service provider system(s) 104 is/are configured to generate and store provider policies that define the service provider's assistance program guidelines. For example, a service provider policy may define types of services that are eligible for assistance, participating providers (e.g., physicians), qualifiers associated with a user's financial situation, insurance coverage/eligibility, or demographic information, and other service provider-specific assistance guidelines. The service provider system(s) 104, and optionally one or more assistance program systems 132, is/are further configured to generate and store assistance program rules for each available assistance program that define each program's criteria for qualification. Non-limiting examples of assistance program rules may define qualifiers associated with income, household size, medical diagnoses, covered services, age, employment status, coverage/enrollment in other assistance programs and/or insurance programs, housing status (e.g., homelessness, low-income/subsidized housing residency), etc.

The third-party data source system(s) 106 tracks and stores information about individuals, such as the user (e.g., the consumer of healthcare services, the guarantor of the consumer's ongoing obligations). Examples of such information include historical transaction profiles providing a credit scores and limits; transaction history and types and frequency of outgoing transactions (e.g., purchases, expenses, outgoing alimony) related to revolving credit; incoming transaction (e.g., wages, salary, received alimony) records, and asset records. The third-party data source systems 106 also may track and store demographic information about individuals and communities that are useful for performing analytics about an individual or a population of individuals. Examples of such demographic information include the number of dependents/children, employers, education level, age, marital status, housing status, etc. The third-party data source systems 106 additionally may track and store coverage-related information about individuals, such as enrollment in assistance programs or enrollment in insurance programs.

The data processor system 110 is in communication with the service provider system(s) 104, the third-party data system(s) 106, the user's computing device 102, and optionally the third-party assistance program system(s) 132. The exchange of data and interaction between these systems of the example operating environment 100 is explained in more detail herein.

Figure 1B:
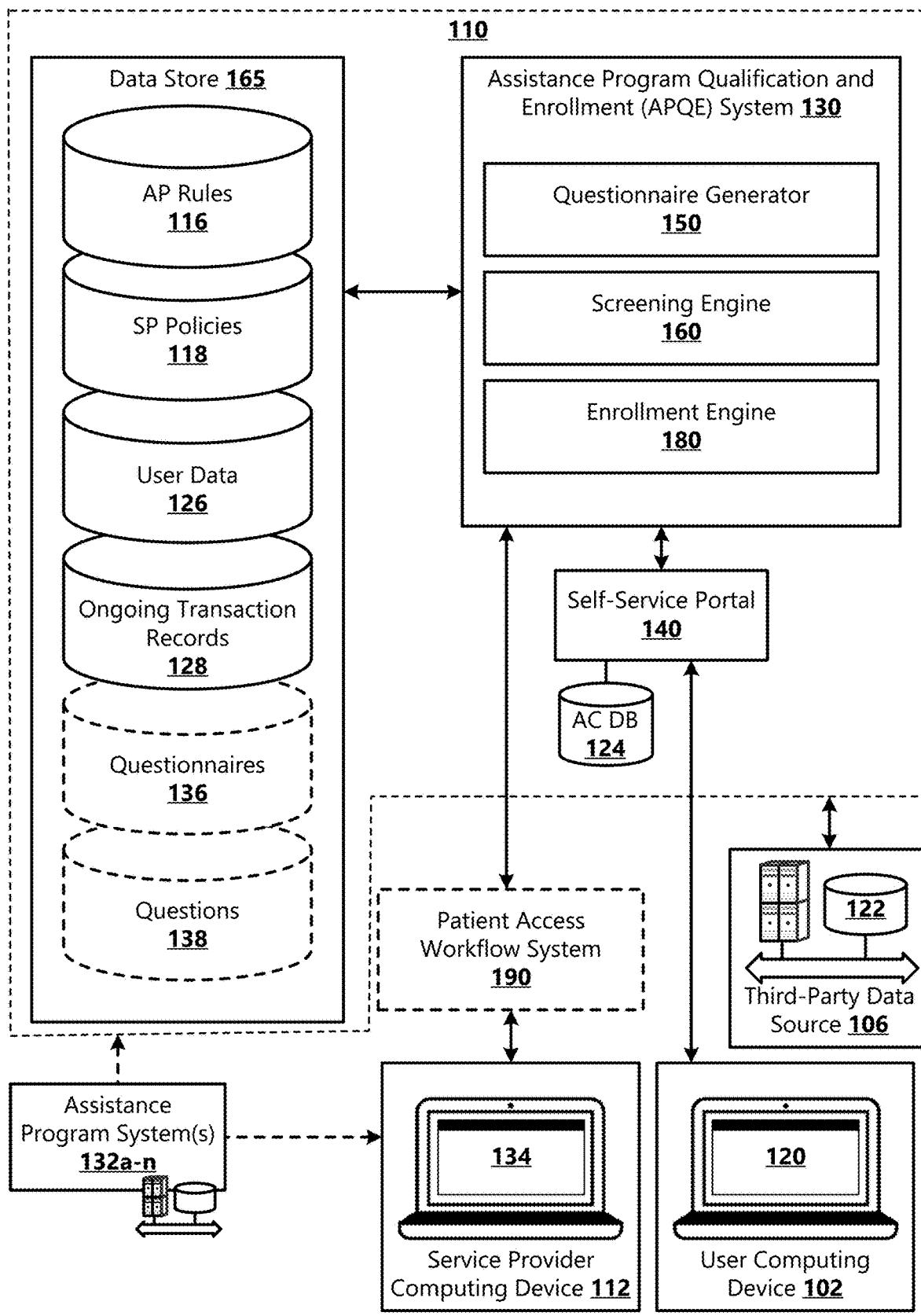
FIG. 1B is a block diagram illustrating an example embodiment of an assistance program qualification and enrollment system.

FIG. 1B is a block diagram illustrating an example embodiment of an assistance program qualification and enrollment (APQE) system 130 that is executed by the data processor system 110. In this example, the data processor system 110 includes an APQE system 130, a self-service portal system 140, and a data store 165. According to an aspect, the APQE system 130 includes a questionnaire generator 150, a screening engine 160, and an enrollment engine 170. Instructions for the APQE system 130 can be executed by a single computing device 112. Alternatively, instructions for the APQE system 130 can be distributed across two or more computing devices that are in communication with each other and form a part of the data processor system 110.

The data store 165 can include memory that forms a part of a computing device or devices executing the APQE system 130. Alternatively, the data store 165 can include separate or secondary storage hardware in communication with the computing device executing the APQE system 130. In various examples, the data store 165 can be a cloud-based storage system that is separate and remote from the data processor system 110, but is in communication with the data processing system 110 through the network 108. As will be described in more detail below, the data store 165 stores user data 126 about the user, ongoing transaction records 128 for which the user is responsible, assistance program rules 116, service provider policies 118, and in some implementations, pre-generated questionnaires 136 for the user and pre-generated questions 138 for inclusion in a questionnaire. In some example aspects, the data store 165 stores one or more forms, such as application or enrollment forms, that can be automatically filled with collected and received data and that can be exposed to the user via a self-service portal 140.

The self-service portal 140 is illustrative of a secure web-based application platform that can be accessed by a user agent (e.g., a web browser or a stand-alone application) executing on the user computing device 102. According to an aspect, the self-service portal 140 provides authenticated users with access to information related to the user (e.g., the user or a consumer associated with the user). For example, the user can use the self-service portal 140 for one or a combination of the following activities: to see ongoing transaction information associated with one or more service provider account(s), to make online payments or set up payment plans, to schedule appointments, and, according to an aspect of the present disclosure, to qualify for and enroll in an assistance program. In various implementations, the types of information available to users via the self-service portal 140 may be defined by the service provider(s).

In example aspects, the self-service portal 140 is configured to generate a self-service portal user interface (UI) 120 for display on the user computing device 102 via the user agent. According to an aspect, the self-service portal 140 includes one or more application programming interfaces (APIs), which connect the self-service portal 140 to the APQE system 130 so that the self-service portal is able request an assistance program qualification questionnaire from the APQE system and to transmit data input by the user via the user computing device 102 to the APQE system for determining whether the user qualifies for an assistance program and to communicate that determination to the user.

In various examples, the self-service portal 140 includes or is in communication with an access control engine that is configured to authenticate the user using a suitable authentication technology. For example, to access secure user-related content, the self-service portal 140 may require the user to input identifying information to prove that the user is who he/she says that he/she is and to determine what information the user is authorized to access. The access control engine may be configured to verify the identifying information provided by the user against identifying information stored in an access control database 124 for verifying the user's identify. When the user's identify is successfully authentication, the access control engine may be further configured to request the user's access privileges against an authorization policy or set of permissions stored in the access control database 124 for determining what information the user is authorized to access. The access control engine may be a single system that is configured to perform authentication and authorization processes; or, the access control engine may include separate authentication and authorization engines, wherein the authentication is configured to perform authentication processes and the authorization engine is configured to perform authorization processes. Likewise, the access control database 124 may be a single database or separate databases.

According to an aspect, the self-service portal 140 is configured to invoke a questionnaire API to request a questionnaire comprising a set of qualification questions from the questionnaire generator 150 to transmit to the user computing device 102. In example aspects, the self-service portal 140 is configured to request the set of qualification questions from the questionnaire generator 150 responsive to receiving a request for or a selection of assistance program options. For example, the request for or a selection of assistance program options may be user-initiated request/selection initiated via a user input or user selection via the self-service portal UI 120.

The questionnaire generator 150 is illustrative of one or more software applications, modules, or computing devices operative or configured to generate a questionnaire for acquiring information needed to make an assistance program qualification determination. In example aspects, the questionnaire includes the set of qualification questions that are customized to the user based at least in part on a user profile and the service provider associated with the user. In some example aspects, the questionnaire generator 150 generates the questionnaire dynamically responsive to receiving a request for a set of qualification questions from the self-service portal 140. In other example aspects, the questionnaire generator 150 proactively generates the questionnaire responsive to receiving an ongoing transaction record 128 associated with a service provided to a user, and stores the questionnaire in the data store 165. Accordingly, when a request is received for the questionnaire, the questionnaire generator 150 is configured to retrieve the pre-generated questionnaire 136 from the data store 165.

According to an aspect, as part of generating the questionnaire, the questionnaire generator 150 is configured to determine data needed to make a determination as to whether the user qualifies for one or more assistance programs. This data is herein referred to as qualification data. As part of determining what qualification data is needed for determining the user's qualification for assistance with one or more ongoing transaction records 128, the questionnaire generator 150 is configured to access the data store 165 to retrieve assistance program rules 116 associated with one or more assistance programs and service provider policies 118 for generating the questionnaire based on qualification criteria for the assistance programs. In some examples, the questionnaire generator 150 may receive user identifier information and optionally service provider identifier information from the self-service portal 140. This information may be determined by the self-service portal 140 as part of the log-in process. According to an aspect, the questionnaire generator 150 is configured to access the data store 165 to retrieve ongoing transactions records 128 associated with the user. As described above, ongoing transaction records 128 are provided by the one or more service provider systems 104, and each ongoing transaction record includes information related to a service or services provided to that user by the service provider. Based on which service providers the user has ongoing transaction records 128 with, the questionnaire generator 150 is configured to retrieve those service provider policies 118. For example, a single healthcare service encounter may include multiple services provided to the user by multiple service providers, such as a hospital, a physician, a lab, a radiology service, etc.; and an ongoing transaction record may be associated with each of these services.

As described above, a service provider policy 118 defines the service provider's assistance program guidelines. In example aspects, service provider policies 118 are generated by and received from the one or more service provider systems 104. In other example aspects, service provider policies 118 are generated by the APQE system 130 based on guidelines provided by the service provider system(s) 104. The service provider policies 118 may be stored as a set of rules that define specific data to evaluate and an action to be taken when the rule is evaluated as true. Based on the specific data to be evaluated according to specific service provider policy 118 rules, the questionnaire generator 150 determines what qualification data is needed to make a qualification determination.

As part of determining the qualification data for a qualification determination, the questionnaire generator 150 is further configured to access the data store 165 to retrieve assistance program rules 116 associated with one or more assistance programs for generating the questionnaire based on qualification criteria for the assistance programs. In example aspects, the assistance program rules 116 are generated by and received from the one or more service provider systems 104 and/or one or more assistance program systems 132. In other example aspects, the assistance program rules 116 are generated by the APQE system 130 based on assistant program eligibility criteria provided by the service provider system(s) 104 and/or the assistance program system(s). For example, APQE system 130 is utilized to pre-qualify/qualify the user for and enroll the user in an assistance program from assistance program providers who are part of or who have contracted with the healthcare service provider (or a third-party provider of a patient access workflow system 190 utilized by the healthcare service provider system 104). The assistance program rules 116 may be stored as rules that define specific data to evaluate and an action to be taken when the rule is evaluated as true. Based on the specific data to be evaluated according to specific assistance program rules 116, the questionnaire generator 150 determines needed qualification data for a qualification determination. In some examples, a service provider policy 118 may define which assistance programs may be permissible for assistance with satisfaction of an ongoing transaction record 128. Accordingly, if a service provider policy 118 defines certain acceptable assistance programs (e.g., service provider-approved assistance programs, assistance programs that have contracted with the service provider) or defines certain unacceptable assistance programs, the questionnaire generator 150 is configured to retrieve the assistance program rules 116 that correspond to the provider policy 118.

One example of an assistance program that may be offered by a service provider or a third-party assistance program can include a charity care program, where users with a family income at a particular percentage below the federal poverty guidelines (e.g., 300% below the federal poverty guidelines) are eligible for 100% charity care. Another example of an assistance program can include a financial assistance program, where users with a family income above the charity care program income qualifier percentage amount, but not exceeding another particular percentage of the federal poverty guidelines (e.g., between 300% and 500% of the federal poverty guidelines) are eligible for discounted care (e.g., a certain percent discount, a certain discounted amount, at an amount generally billed to government program beneficiaries). An example of an assistance program rule 116 associated with either of these assistance programs may define an evaluation of a family income value and a federal poverty guidelines value (e.g., the federal poverty guidelines value may be based on a number of people in the user's household and of which state the user is a resident). Accordingly, based on this assistance program rule 116, the questionnaire generator 150 may determine that qualification data needed to evaluate this rule for making a qualification determination include: the user's family income amount, the user's household size, and the user's state of residency.

When qualification data needed to make a qualification determination for one or more available assistance programs are determined (e.g., based on available assistance program rules 116 and the service provider policies 118 rules corresponding to the service providers associated with the user's ongoing transaction records 128), the questionnaire generator 150 is further configured to obtain one or more qualification data items from one or more data sources. According to an aspect, the questionnaire generator 150 is configured to access the data store 165 to retrieve qualification data stored as user data 126 associated with the user.

In example aspects, user data 126 can include data collected by and received from the service provider system 104, and can include data collected as part of a registration process for the user and data produced as part of providing services to the user. For example, user data 126 can include demographic data about the user, such as but not limited to: first name, middle name/initial, last name, address, telephone number, email address, birthday, age, race, ethnicity, social security number, marital status, employer information, spouse information, etc. User data 126 can further include health-related information, such as but not limited to: patient type (e.g., outpatient, inpatient, emergency department, urgent care), healthcare coverage information, healthcare providers involved in the user's care, etc. In some implementations, user data 126 can include additional patient- and provider-reported health data, such as information associated with diagnoses, medications, family medical history, lab and test results, biometric data, treatment history, etc. One or more types of user data 126 may be collected and used for assistant program qualification determinations based on permissions provided by the user. Other types of user data 126 are possible and are within the scope of the present disclosure.

The questionnaire generator 150 is further configured to access one or more third-party data sources 106 to retrieve qualification data stored as financial data 122 associated with the user. According to an example aspect, the questionnaire generator 150 invokes an API of the third-party data source 106 to locate, access, and extract particular financial data 122. For example, the API connects the questionnaire generator 150 to the third party data source 106 so that the questionnaire generator is able to access financial data 122, which can used by the questionnaire generator as qualification data. The questionnaire generator 150 may request particular financial data 122 related to the qualification data determined to be needed for making a qualification determination for an assistance program. Financial data 122 can include credit history data, a credit score, debt-to-income ratio data, credit utilization data, income data, financial resource data, financial obligation data, etc. Other types of financial data 122 are possible and are within the scope of the present disclosure.

According to example aspects, the questionnaire generator 150 is configured to perform a pre-qualification determination, wherein one or more assistance program rules 116 and service provider policy 118 rules are applied to the collected user data 126 and financial data 122. For example, assistance program rules 116 associated with an assistance program can be used by the questionnaire generator 150 to evaluate whether the collected user data 126 and financial data 122 satisfy qualification criteria for the assistance program; and service provider policy 118 rules associated with a service provider with whom the user has an ongoing transaction record 128 can be used by the questionnaire generator 150 to enforce the service provider's financial assistance policy. The pre-qualification determination results can include one or more assistance programs that the user qualifies for, one or more assistance programs that the user does not qualify for, and/or one or more assistance programs that the user may qualify for but that additional qualification data are needed for making the qualification determination. For example, the one or more assistance programs that the user qualifies for can be added to a list of assistance program candidates for the user. The one or more assistance programs that the user does not qualify for may be removed from consideration and accordingly, additional qualification data may not be requested for those assistance programs.

For an assistance program that the user may qualify for but that additional qualification data are needed for making the qualification determination, the questionnaire generator 150 is configured to determine what qualification data may be missing from the collected user data 126 and financial data 122, and to generate or obtain one or more questions directed to the user for ascertaining additional qualification data that correlate with the missing data. For example, each question may be directed to specific additional qualification data that are needed for making a determination whether qualification criteria for an assistance program are satisfied and to enforce the service provider's financial assistance policy. For example, it may be determined that user household size information is a data item or attribute that can be evaluated as part of determining the user's yearly income and how it compares against the Federal Poverty Guidelines for determining whether the user qualifies for a particular (or more than one) assistance program; and it may be determined that the user household size information is not included in the user's user data 126 nor financial data 122.

Accordingly, the questionnaire generator 150 may generate or access the data store 165 to select a question 138 that requests the user's input for a response defining the user's household size, and may include that question in a questionnaire directed to the user.

Pre-generated questions 138 may be associated with particular assistance program qualification criteria. For example, if a particular assistance program offers financial assistance to users who meet qualification criteria associated with a particular household size, gross annual household income, and assets (e.g., bank or retirement account assets), three questions 138 may be pre-generated for that assistance program and stored: a first question directed to requesting a user response defining the user's household size, a second question directed to requesting a user response defining the user's gross annual household income, and a third question directed to requesting a user response defining the user's assets. In some implementations, the questions 138 are configured with particular selectable responses (e.g., a drop-down box/selectable options of household size choices, gross annual household income ranges, and asset range amounts). According to aspects, the questionnaire generator 150 is further configured to include one or more questions 138 associated with needed/missing qualification data in a questionnaire, and to transmit the questionnaire to the self-service platform 140 for display to the user. In some example aspects, the questionnaire is stored in the data store 165. As should be appreciated, the terms "question" and "questions" are used herein to describe a word or phrase that can be displayed to the user so as to elicit specific information from the user. That is, questions 138 is not limited to interrogative expressions.

According to aspects, the questionnaire includes a reduced set of questions 138. That is, by first determining the qualification data needed to make a qualification determination for the user; accessing available data sources (e.g., user data 126, financial data 122) to determine what of that qualification data is already available; applying the assistance program rules 116 and service provider policy 118 rules to the already-available qualification data for determining which assistance programs the user pre-qualifies for, which assistance programs that the user does not qualify for, and which assistance programs the user may qualify for but that additional qualification data is need to make the qualification determination, the number of questions 138 is reduced to a minimized number of questions to obtain only the additional qualification data needed to make the qualification determination. This, in addition to other benefits, reduces the amount of data input by the user, decreases or eliminates a transmission of sensitive data (e.g., financial data, medical-related data), and can improve the user experience (e.g., by simplifying the financial assistance application process for the user).

In various implementations, the questionnaire generator 150 is configured to receive a request for the questionnaire from the self-service portal 140. For example, the questionnaire generator 150 can provide a questionnaire API and instructions (e.g., markup language code, scripting language code, functions) for the self-service portal 140 to request the questionnaire from the questionnaire generator 150. Responsive to the request, the questionnaire generator 150 responds to the request with an API response that includes the questionnaire and instructions for enabling the self-service portal 140 to generate a UI 120 including the questionnaire (e.g., the set of questions 138 for obtaining the additional qualification data needed to make the qualification determination). In example aspects, the API response includes instructions that define the layout of the questionnaire, and may support different user computing device 102 form factors (e.g., mobile, table, desktop). In various aspects, the UI 120 displayed to the user includes the questionnaire and input controls (e.g., fillable data fields, checkboxes, drop-down lists, or selectable buttons) that enable the user to enter user input in response to the one or more questions 138 included in the questionnaire.

In example aspects, the screening engine 160 provides/exposes a screening API, which the self-service portal 140 can invoke to communicate the user responses (to the questions 138 included in the questionnaire) to the screening engine 160 as part of a request for assistance program qualification results. For example, the screening engine 160 includes one or more APIs, which connect the self-service portal 140 to the screening engine 160 so that the self-service portal is able request assistance program qualification results from the screening engine, to transmit data input by the user via the user computing device 102 to the screening engine for determining whether the user qualifies for an assistance program, and to receive the determination results in an API response from the screening engine.

In example aspects, the screening engine 160 is illustrative of one or more software applications, modules, or computing devices operative or configured to receive user responses to the questions 138 included in the questionnaire, wherein the user responses include the additional qualification data needed to make one or more assistance program qualification determinations for the user, and to apply one or more assistance program rules 116 and service provider policy 118 rules to the received additional qualification data (i.e., user response data), user data 126, and financial data 122 to determine whether the qualification data (i.e., user response data, user data 126 and financial data 122) satisfy qualification criteria for one or more assistance programs.

In various aspects, as part of determining whether the user qualifies for an assistance program, the screening engine is further configured to determine a level or amount of assistance an assistance program may provide. For example, assistance program rules 116 can define specific actions to take when qualification criteria for an assistance program are met. One example of a specific action can include an instruction to approve the user for qualification for the assistance program and to apply a particular percentage discount or a particular dollar amount discount to an owed/obligation amount included in an ongoing transaction record 128 for the user. The discounted obligation amount can be included in a qualification determination result.

In some example aspects, the screening engine 160 is further configured to rank the qualification determination results based on the discounted obligation amounts. For example, based on an application of assistance program rules 116 and service provider policy 118 rules to the user response data, user data 126, and financial data 122, the screening engine 160 may determine that the user qualifies for two assistance programs. A first assistance program qualification determination result may indicate that the user qualifies for a 50% discount of the user's obligation amount (e.g., $1000), resulting in a discounted obligation amount of $500. A second assistance program qualification determination result may indicate that the user qualifies for a 75% discount of the obligation amount, resulting in a discounted obligation amount of $225. The screening engine 160 may rank these two qualification determination results based on the discounted obligation amounts such that the second qualification determination result is ranked higher than the first qualification determination result.

According to an aspect, the screening engine 160 is configured to generate an assistance program qualification results response based on the qualification determination result(s) for the user. For example, responsive to the assistance program qualification results request, the screening engine 160 responds to the request with an API response that includes assistance program qualification results and instructions for enabling the self-service portal 140 to generate a UI 120 including an indication of whether the user qualifies for an assistance program and if the user qualifies for an assistance program, input controls that enable the user to select and enroll in the assistance program for which the user is qualified. In example aspects, the API response includes instructions that define the layout of the results feedback, and may support different user computing device 102 form factors (e.g., mobile, table, desktop).

According to an example aspect, the assistance program qualification results response includes a listing of assistance programs that the user qualifies for in association with a particular ongoing transaction record 128. For example, if the user has multiple ongoing transaction records 128, the user may qualify for one or more assistance programs for one or more of the individual ongoing transaction records. According to another example aspect, the assistance program qualification results response includes a ranked listing of assistance programs for which the user qualifies, including the discounted obligation amounts. In some implementations, if the user qualifies for more than one assistance program for a particular ongoing transaction record 128, the screening engine 160 is configured to include only the highest ranked assistance program in the assistance program qualification results response. For example, if the user qualifies for a first assistance program that offers a 50% discount and also qualifies for a second assistance program that offers a 100% discount, only the second assistance program may be included in the assistance program qualification results response.

In some examples, enrollment in one assistance program may conflict with enrollment in another assistance program based on certain assistance program rules 116 and/or service provider policies 118. In such cases, the screening engine 160 is configured to include instructions in the assistance program qualification results response that enable the self-service portal 140 to prevent conflicting enrollment selections. For example, if the user selects to enroll in a first assistance program and that program does not allow for enrollment in another assistance program, the self-service portal 140 can execute the instructions to disable input controls for selecting and enrolling in other (conflicting) assistance programs.

In example aspects, if the user does not qualify for an assistance program, the assistance program qualification results response includes a notification that the user does not qualify for an assistance program. In another example aspect, if the user does not qualify for an assistance program, the assistance program qualification results response includes a link to a settlement plan system configured to provide a settlement plan for the user to settle according to a schedule over a period of time.

The enrollment engine 170 is illustrative of one or more software applications, modules, or computing devices operative or configured to receive a request for enrollment in one or more assistance programs from the self-service portal 140. In example aspects, the enrollment engine 170 provides/exposes an enrollment API, which the self-service portal 140 can invoke to communicate an enrollment selection to the enrollment engine 170 as part of a request for automated enrollment in an assistance program. For example, the screening engine 160 includes one or more APIs, which connect the self-service portal 140 to the enrollment engine 170 so that the self-service portal is able send enrollment selections and the enrollment request.

The enrollment engine 170 is configured to receive the request for enrollment in one or more selected assistance programs. According to some aspects, the enrollment engine 170 includes a set of code that evaluates the assistance program rules 116 and the service provider policy 118 rules associated with enrollment criteria for the selected assistance programs against data previously collected for the user (user data 126, financial data 122, and user response data) for determining whether supplementary data is needed to enroll the user in the one or more assistance programs. For example, supplementary data can include additional user input data and/or supporting documents.

Assistance program rules 116 can define specific actions to take when qualification criteria for an assistance program are met and the user selects to enroll in the assistance program. For example, assistance program rules 116 may define an action to provide information to the user associated with completing the enrollment process. One example of a specific action can include an instruction to request certain additional user input (e.g., user signature, demographic data, financial data, health-related data) or particular supporting documents (e.g., bank statements, tax documents, income documents) from the user. For example, the rule action can include an instruction to include one or more additional questions 138 and/or a document upload interface in an API response to the self-service portal 140.

In example aspects, the enrollment engine 170 is configured to generate an enrollment response based on the result(s) of additional user input determination(s). For example, responsive to the enrollment request, the enrollment engine 170 responds to the request with an API response that includes instructions for enabling the self-service portal 140 to generate a UI 120 including instructions for completing enrollment (e.g., instructions associated with additional user input or particular supporting documents needed from the user to complete the enrollment process for one or more selected assistance programs) and input controls (e.g., fillable data fields, checkboxes, drop-down lists, or selectable buttons) that enable the user to enter additional user input (e.g., user signature, demographic data, financial data, health-related data) and/or a document upload interface that enables the user to upload and transmit supporting documents (e.g., bank statements, tax documents, income documents) to the enrollment engine 170.

In some example aspects, the enrollment engine 170 is configured to access one or more forms, such as application or enrollment forms corresponding to the one or more selected assistance programs, to pre-fill one or more fields of the one or more forms with previously collected for the user (user data 126, financial data 122, and user response data), and include the form with unfilled fields in the enrollment response. In example aspects, the API response includes instructions that define the layout of the instructions, input controls, and/or document upload interface, and may support different user computing device 102 form factors (e.g., mobile, table, desktop).

According to an aspect, the enrollment engine 170 is further configured to receive inputs entered into the self-service portal 140 by the user (e.g., user signature, demographic data, financial data, health-related data, supporting documents). For example, the enrollment engine 170 provides/exposes an API, which the self-service portal 140 can invoke to communicate user inputs to the enrollment engine 170 for completing the user's enrollment in one or more assistance programs.

Another example of a specific action defined by assistance program rules 116 can include an instruction to communicate an enrollment request to one or more of the assistance program system(s) 132, the service provider system(s) 104, and a patient access workflow system 190 associated with a service provider system. In various examples, the service provider system 104 may utilize a patient access workflow system 190 to perform one or more patient access workflow processes. An example of a patient access workflow system 190 includes the eCare NEXT® platform, available from EXPERIAN HEALTH, INC. of Franklin, Tenn. The patient access workflow system 190 may be implemented on a computing device (e.g., server computing device, a cloud-based server computing device, desktop computing device) of the service provider system 104 or in communication with the service provider system.

According to an aspect, the enrollment engine 170 is configured to execute the specific action and communicate the user's enrollment request to the corresponding assistance program system(s) 132, the corresponding service provider system(s) 104, and/or patient access workflow system 190. In some example aspects, the enrollment engine 170 invokes an API of the assistance program system(s) 132 and/or the service provider system(s) 104 to enroll the user in an assistance program. For example, the API connects the enrollment engine 170 to the assistance program system(s) 132, service provider system(s) 104, and/or patient access workflow system 190 associated with the provider system(s) so that the enrollment engine 170 is able to transmit an indication of the user's selection to enroll in an assistance program and associated data (e.g., user data 126, financial data 122, user inputs, supporting documents) to the corresponding assistance program system(s) 132, service provider system(s) 104, and in some examples, a patient access workflow system 190 associated with the provider system(s). Aspects of the APQE system 130 enable the user to gather and transmit sensitive supporting documents only when the user knows that he/she qualifies and has selected to enroll in an assistance program. As can be appreciated, this can improve data security, computing resources associated with uploading and transmitting the documents, and the user experience.

According to an aspect, the enrollment engine 170 is configured to receive an indication of completion of the assistance program application and enrollment process from one or more of the assistance program system(s) 132, service provider system(s) 104, and patient access workflow system 190. Responsive to receiving the indication of completion, the enrollment engine 170 may update the data store 165 with an assistance program application and enrollment process status update. For example, the status of the user's assistance program application for and enrollment in an assistance program can be stored by the APQE system 130. In various examples, the ongoing transaction records 128 for the user may be updated with discounted obligation amounts. Accordingly, when the user uses these self-service portal 140 to view his/her obligations for services, the self-service portal obtains the updated discounted obligation amounts for display to the user. In some examples, the enrollment engine 170 may be configured to communicate the completion of the assistance program application to the user via the self-service portal 140 or via one or more other communication means (e.g., text message, email, phone call, mail).

Figure 2A:
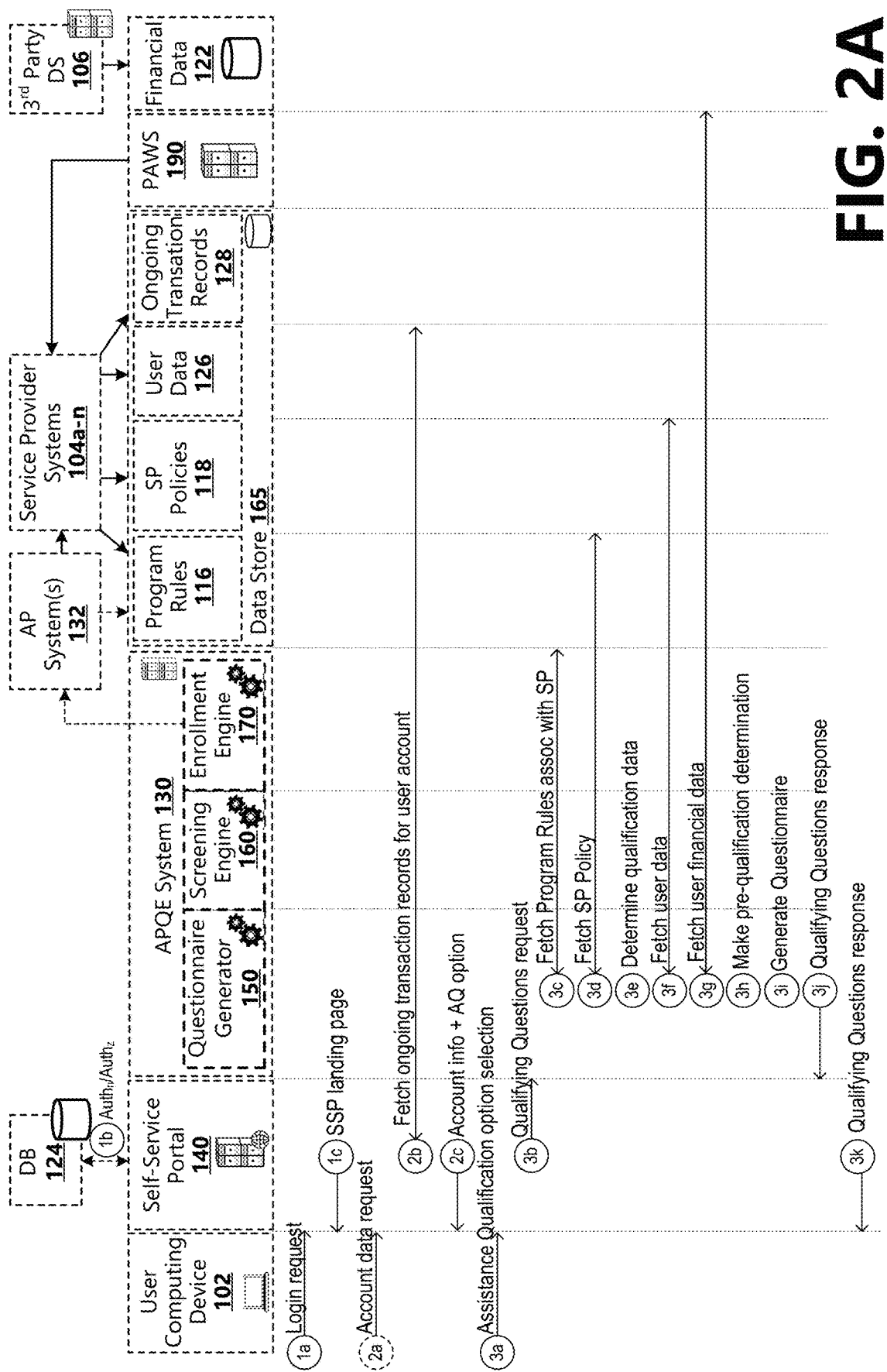
FIGS. 2A-B are data flow charts illustrating example processes and communications between operating environment for providing automated assistance program qualification and enrollment according to an embodiment.
Figure 2B:
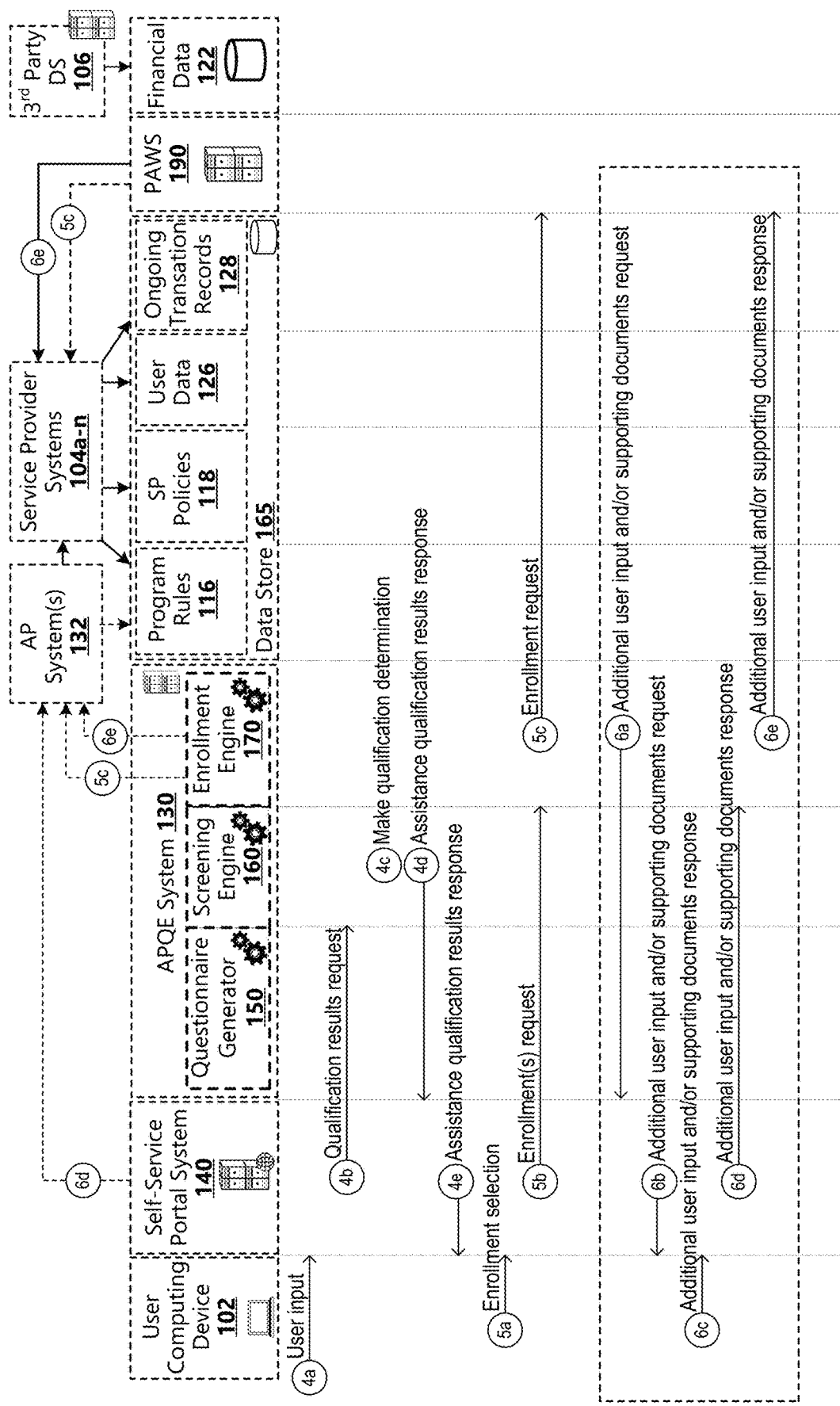

FIGS. 2A-B are sequence diagrams illustrating example processes and communications various components of the operating environment 100 for providing automated assistance program qualification and enrollment according to an embodiment. In FIGS. 2A-B, various arrows are labeled with circled numerals indicative of an example flow of data and/or operations among the components. As should be appreciated, some messages can be exchanged out of the order (e.g., substantially concurrently or in reverse order) as shown in FIGS. 2A-B.

With reference now to FIG. 2A, 1a is illustrative of a login request. For example, the user may access the self-service portal 140 via a webpage or an application, and may be presented with data input fields to enter identifying information, such as a username and password, or may be enabled to use other input options (e.g., fingerprint scanner, camera, microphone) for inputting biometric data (e.g., fingerprint, image of face, voiceprint) to log into the self-service portal 140. Other login methods are possible and are within the scope of the present disclosure. 1b is illustrative of an authentication and authorization process, where the self-service portal 140 accesses an access control database 124 (e.g., using an access control engine) to verify that the user's identity and to determine access control privileges to data that the user has. 1c is illustrative of a landing page or UI 120 presented to the user upon a success authentication. In various examples, the UI 120 includes user input controls for enabling the user to request assistance program options.

Figure 4A:
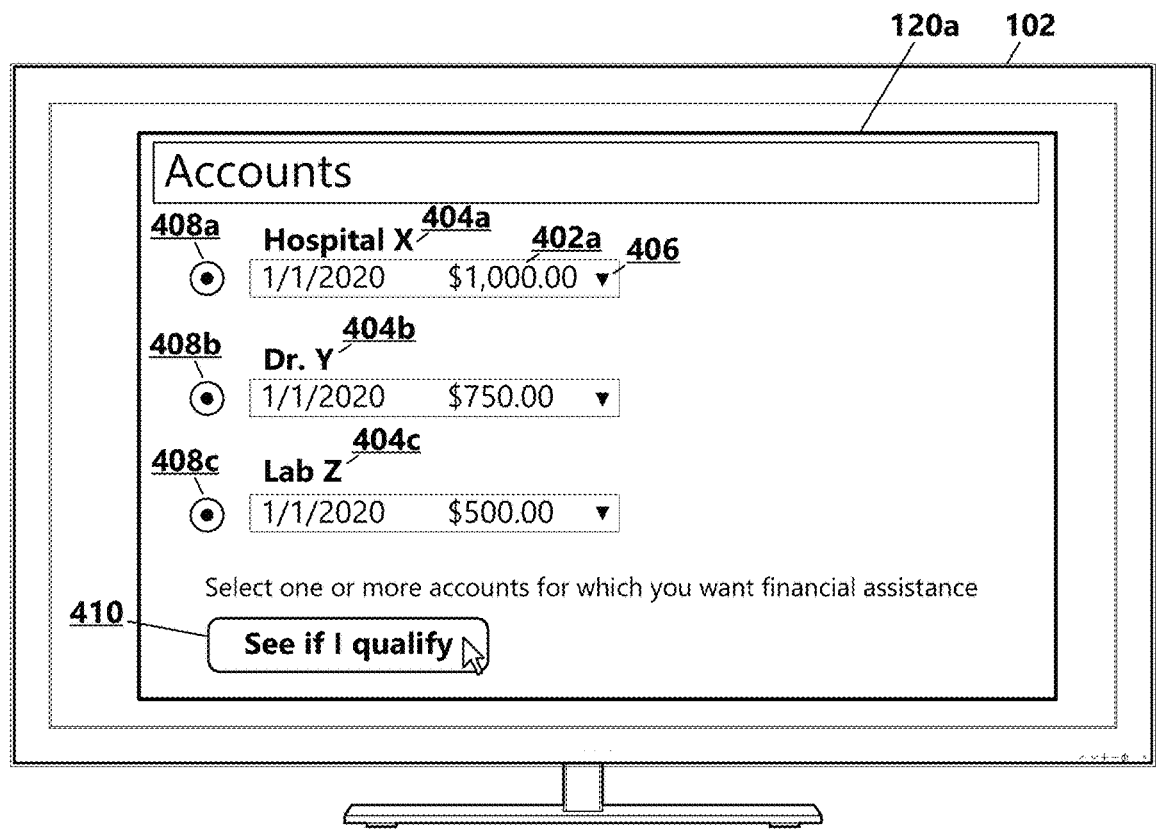
FIG. 4A is an illustration of an example user interface including a listing of a user's ongoing transaction information and an input control for initiating an assistance program qualification process.

2a represents a user-initiated request for user account information (e.g., ongoing transaction records 128). For example, the user may use the self-service portal 140 to view ongoing transaction records 128 associated with one or more service provider account(s), to make online payments or set up payment plans, to schedule appointments, and, according to an aspect of the present disclosure, to qualify for and enroll in an assistance program. The user-initiated request (2a) can be responsive to a selection of an input control, such as an option to view ongoing transaction records 128. In various implementations, the types of information available to users via the self-service portal 140 may be defined by the service provider(s). In some examples, the self-service portal 140 may automatically fetch (communication 2b) certain data that the user is authorized to access (e.g., the user's ongoing transaction records 128) when the user is authenticated. 2b is representative of the self-service portal 140 fetching the user's ongoing transaction records 128 from the data store 165. In some examples, one or more service provider systems 104 may provide a batch of new ongoing transaction records 128 to the APQE system 130, which stores the ongoing transaction records in the data store 165. In other examples, the self-service portal 140 may fetch the user's ongoing transaction records 128 from one or more service provider systems 104 (e.g., via an API request) responsive to a user request (2a) or when the user is authenticated. 2c illustrates a process performed by the self-service portal 140 where the self-service portal generates a UI 120 for display on the user computing device 102 via the user agent, wherein the UI includes obligation amounts associated with the user's ongoing transaction records 128. The UI 120 may further include input controls that enable the user to initiate an assistance program qualification process, wherein the process includes determining whether the user qualifies to receive financial assistance for the one or more obligation amounts. One example of this UI 120 is illustrated in FIG. 4A and is described further below.

3a is illustrative of a user-selection of one or more obligation amounts and/or a selection of an input control to initiate the assistance program qualification process, and 3*b* is illustrative of a self-service portal 140 request directed to the questionnaire generator 150 of the APQE system 130 for a questionnaire comprising a reduced set of questions customized for the user, wherein the questions are generated or selected based on qualification data needed to making one or more qualification determinations. 3*c* represents the questionnaire generator 150 accessing assistance program rules 116 for one or more assistance programs and 3*d* represents the questionnaire generator 150 accessing one or more service provider policies 118. For example, the questionnaire generator 150 accesses the assistance program rules 116 and service provider policies 118 for determining (3*e*), (e.g., from qualification/eligibility criteria defined in the assistance program rules 116 and service provider policies 118) what qualification data is needed to determine the user's qualification for one or more assistance programs.

3*f* is illustrative of the questionnaire generator 150 accessing user data 126 collected by and received from one or more service provider systems 104, wherein the user data include qualification data determined as needed for determine the user's qualification for one or more assistance programs. 3*g* is illustrative of the questionnaire generator 150 requesting and receiving user financial data 122 from one or more third party data sources 106, wherein the financial data include qualification data determined as needed for determine the user's qualification for one or more assistance programs.

Figure 4B:
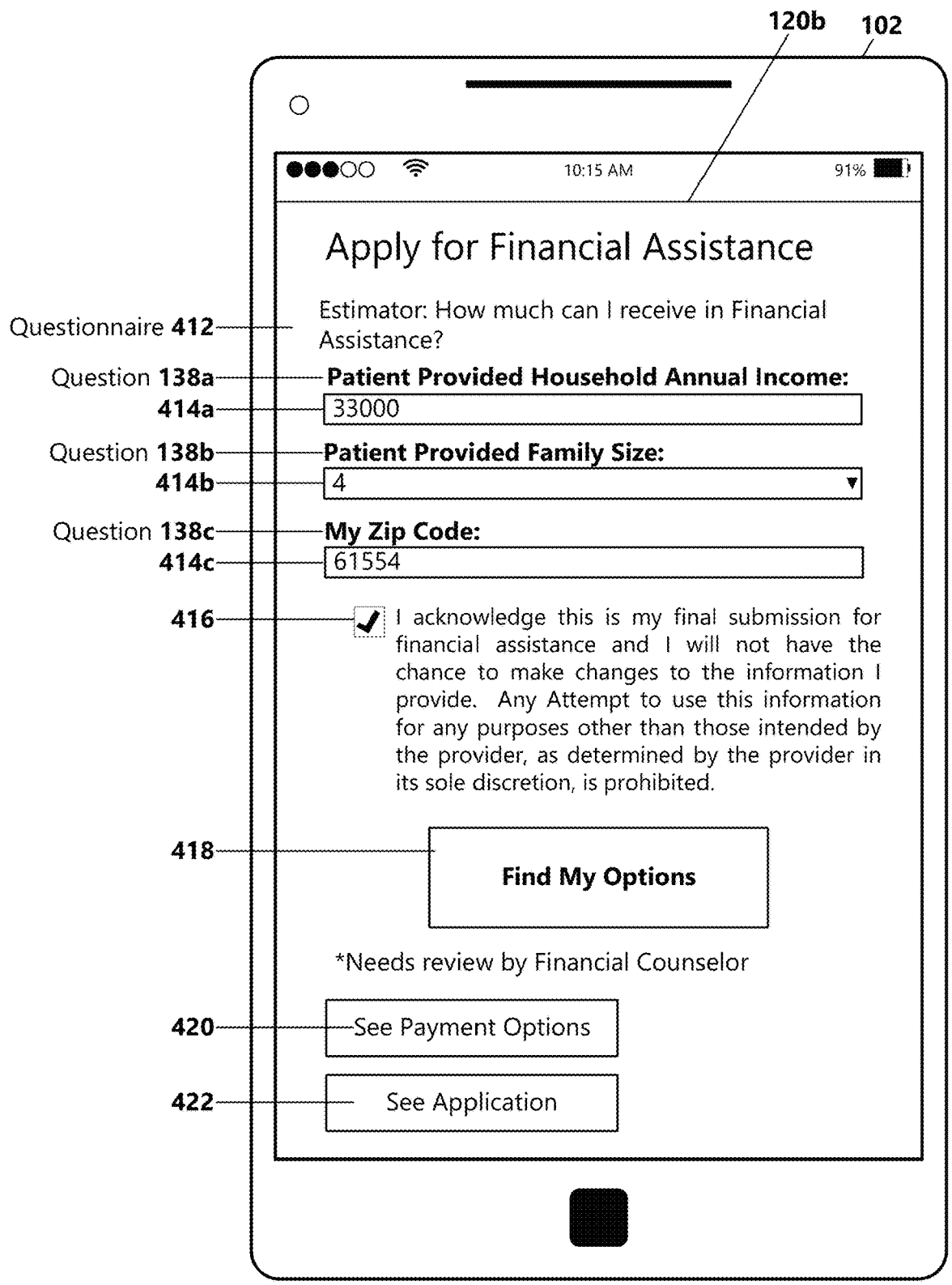
FIG. 4B is an illustration of an example user interface including a set of user-specific questions for obtaining qualification data needed to make a determination regarding the user's qualification to receive assistance for one or more obligation amounts.

3*h* represents a pre-qualification determination process performed by the questionnaire generator 150, where the questionnaire generator evaluates the collected data by applying one or more assistance program rules 116 and service provider policy 118 rules to the collected data for determining one or more of: one or more assistance programs that the user qualifies for, one or more assistance programs that the user does not qualify for, and/or one or more assistance programs that the user may qualify for but that additional qualification data are needed for making the qualification determination. For an assistance program that the user may qualify for but that additional qualification data are needed for making the qualification determination, the pre-qualification determination process further includes the questionnaire generator 150 determining what qualification data may be missing from the collected user data 126 and financial data 122 based on the assistance program rules 116 and service provider policy 118 rules, and to generate (3*i*) a questionnaire including one or more questions 138 directed to the user for ascertaining additional qualification data that correlate with the missing data. 3*j* represents the communication of a response to the self-service portal request (2*b*), wherein the response includes the questionnaire including the one or more questions 138. 3*k* is illustrative of the self-service portal 140 generating a UI 120 including the questionnaire for display on the user computing device 102. One example of this UI 120 is illustrated in FIG. 4B and is described further below.

With reference now to FIG. 2B, 4*a* is illustrative of the self-service portal 140 receiving user input in response to the one or more questions 138 included in the questionnaire, and 4*b* is illustrative of a communicating of the user input/responses/additional qualification data to the screening engine 160 as part of a request for a qualification results request. 4*c* represents a qualification determination process performed by the screening engine 160. For example, as part of the qualification determination process, the screening engine 160 applies one or more assistance program rules 116 and service provider policy 118 rules to the received additional qualification data (i.e., user response data), user data 126, and financial data 122 to determine whether the qualification data (i.e., user response data, user data 126 and financial data 122) satisfy qualification criteria for one or more assistance programs. Results of the qualification determination process can include a listing of assistance programs that the user qualifies for in association with a particular ongoing transaction record 128. In various implementations, the listing is a ranked listing of assistance programs for which the user qualifies and includes determined discounted obligation amounts associated with the financial assistance offered as part of the assistance programs. 4*d* represents a communication of the qualification determination results in a response directed to the self-service portal system 140, and 4*e* is illustrative of the self-service portal 140 generating a UI 120 including the qualification determination results for display on the user computing device 102.

5*a* is illustrative of a user-selection to enroll in one or more assistance programs, 5*b* is illustrative of the self-service portal 140 communicating the user's enrollment selection(s) to the enrollment engine 170, and 5*c* is illustrative of the enrollment engine 170 communicating the user's enrollment selection(s) as part of an enrollment request directed to one or more of the corresponding assistance program system(s) 132, the corresponding service provider system(s) 104, and/or patient access workflow system 190.

Figure 4D:
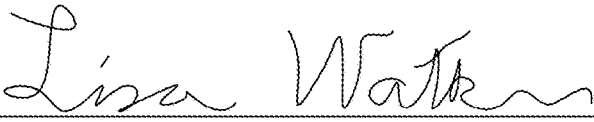

6*a*-6*e* are optional processes/communications that may be performed when certain additional user input (e.g., user signature, demographic data, financial data, health-related data) and/or particular supporting documents (e.g., bank statements, tax documents, income documents) may be needed to complete the enrollment process for an assistance program (e.g., according to assistance program rules 116 and/or service provider policies 118). 6*a* represents a communication of a request directed to the self-service portal 140 for the additional user input and/or supporting documents. In some examples, 6*a* can include a form, such as an application form associated with an assistance program. 6*b* is illustrative of the self-service portal 140 generating a UI 120 including the form and/or instructions to complete the enrollment process. In various examples, the UI 120 can include input controls and/or an interface for enabling the user to provide/upload the additional user input and/or supporting documents. One example of this UI 120 and form 400 is illustrated in FIGS. 4C and 4D and is described further below.

6*c* is illustrative of the user inputting additional user input and/or uploading supporting documents to the self-service portal 140, and 6*d* is illustrative of an optional communication of the additional user input and/or supporting documents to the enrollment engine 170 or directly to an assistance program system 132 (e.g., via an API). 6*e* is illustrative of a communication of the additional user input and/or supporting documents to the assistance program system 132, to the service provider system 104, or to the service provider system via a patient access workflow system 190 associated with the service provider system 104. As should be appreciated, additional communications and processes may be performed by one or more components of the APQE system 130 or by other components in the operating environment 100 that are not represented in FIGS. 2A and 2B. The sequence diagrams illustrated in FIGS. 2A and 2B show one example of the communications and processes involved as part of providing automated assistance program qualification and enrollment in accordance with an embodiment.

Figure 3:
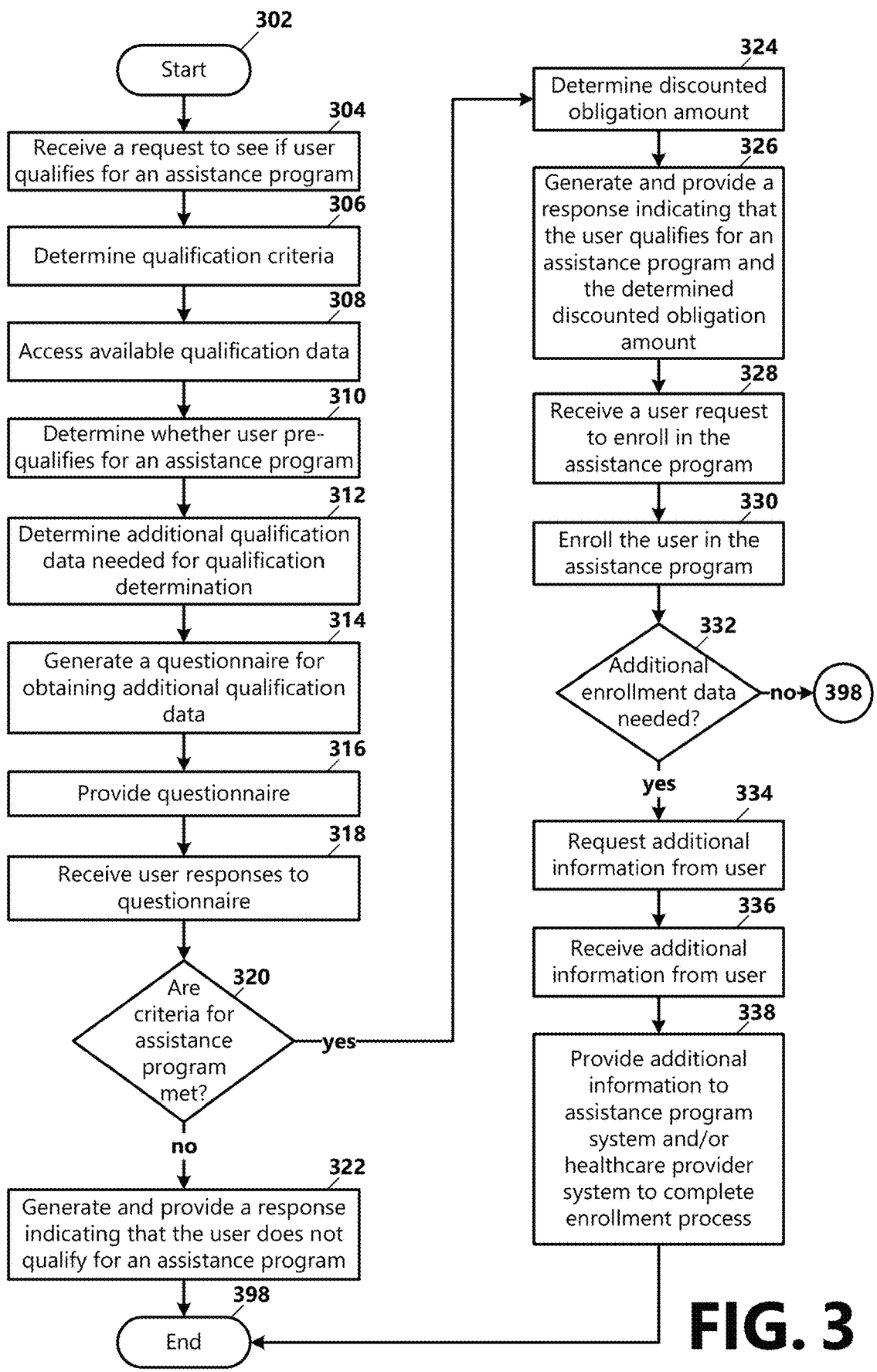
FIG. 3 is a flow chart showing general stages involved in an example method for providing automated assistance program qualification and enrollment according to an embodiment.

FIG. 3 is a flow chart showing general stages involved in an example method 300 for providing automated assistance program qualification and enrollment according to an embodiment. The method 300 begins at START OPERATION 302 and proceeds to OPERATION 304, where the method 300 uses the questionnaire generator 150 of the APQE system 130 to receive a request from the self-service portal 140 to determine whether the user qualifies for an assistance program to discount an obligation amount owed to a service provider for services received from the service provider. In various examples, the qualification request (3b) is received responsive to the user logging into the self-service portal 140, the self-service portal providing an indication of obligation amounts associated with one or more ongoing transaction records 128 related to services received from one or more service providers in a UI 120 for display to the user, and a user-selection to determine whether the user meets criteria for one or more assistance programs. In other example, the qualification request (3b) is automatically generated when an ongoing transaction record 128 for the user is received from a service provider system 104 by the APQE system 130. In an example aspect, the service provider system 104 may send a batch of new ongoing transaction records 128 to the APQE system 130 on a scheduled basis (e.g., daily, nightly, weekly). In another example aspect, the service provider system 104 may send a new ongoing transaction record 128 to the APQE system 130 when the new record is created. According to an aspect, the qualification request (3b) includes information identifying the user and the service provider associated with the ongoing transaction record 128.

At OPERATION 306, the method 300 uses the questionnaire generator 150 to determine qualification data associated with qualification criteria for one or more assistance programs offered by one or more assistance program providers who are part of the healthcare service provider, one or more assistance program providers who have contracted with the healthcare service provider, or one or more third-party assistance program providers. In example aspects, the questionnaire generator 150 accesses assistance program rules 116 for available assistance programs and service provider policy 118 rules for the service providers associated with the user's ongoing transaction records 128 for determining qualification criteria for the assistance programs. For example, the qualification criteria can be defined in conditions (e.g., if statements) of the assistance program rules 116 and service provider policy 118 rules.

At OPERATION 308, the method 300 uses the questionnaire generator 150 to access available qualification data associated with the qualification criteria. For example, the user data 126 can be provided by one or more service provider systems 104 prior to the qualification request (3b) and stored in the data store 165, or can be provided by a service provider system responsive to a request for the user data. The financial data 122 can be requested from (e.g., via an API call to) a third-party data source 106.

At OPERATION 310, the method 300 uses the questionnaire generator 150 to apply the assistance program rules 116 and service provider policy 118 rules to the user's user data 126 and financial data 122 for one or more of: one or more assistance programs that the user qualifies for, one or more assistance programs that the user does not qualify for, and/or one or more assistance programs that the user may qualify for but that additional qualification data are needed for making the qualification determination.

For an assistance program that the user may qualify for but that additional qualification data are needed for making the qualification determination, at OPERATION 312, the method 300 uses the questionnaire generator 150 to determining what qualification data may be missing from the collected user data 126 and financial data 122 based on the assistance program rules 116 and service provider policy 118 rules. For example, the additional qualification data needed to make the qualification determination(s) may include certain information that may not be included in the collected user data 126 and financial data 122, information that may need to be updated or verified by the user, or inconsistent data (e.g., different names for the user in user data 126 and/or financial data 122).

At OPERATION 314, the method 300 uses the questionnaire generator 150 to generate a questionnaire including one or more questions 138 directed to the user based on the additional qualification data needed for making the qualification determination. The one or more questions 138 can be pre-generated questions or can be generated dynamically.

At OPERATION 316, the method 300 uses the questionnaire generator 150 to provide the questionnaire to the self-service portal 140 for display to the user. In various examples, the questionnaire is provided to the self-service portal 140 in an API response (3j) to a request for the questionnaire or the qualification request (3b).

In response to the self-service portal 140 generating and displaying a UI 120 including the questionnaire, receiving user input/responses (4a) to the questions 138 via the UI, and sending those user input/responses (4a) to the screening engine 160 (e.g., as part of a qualification results API request (4b)), at OPERATION 318, the method 300 uses the screening engine 160 to receive the additional qualification data included in the user input/responses (4a).

At DECISION OPERATION 320, the method 300 uses the screening engine 160 to make one or more qualification determinations (4c). For example, at DECISION OPERATION 320, the screening engine 160 applies one or more assistance program rules 116 and service provider policy 118 rules to the received additional qualification data (i.e., user response data), user data 126, and financial data 122 to determine whether the qualification data (i.e., user response data, user data 126 and financial data 122) satisfy qualification criteria for one or more assistance programs.

When a determination is made that the qualification data do no satisfy qualification criteria for an assistance program, at OPERATION 322, the method 300 uses the screening engine 160 to generate and communicate a response (4d) to the self-service portal 140 that indicates that the user does not qualify for an assistance program. In various examples, in the response (4d), the screening engine 160 may include a link to a settlement plan system, which the user can navigate to request a settlement plan for settling an obligation according to a schedule over a period of time.

When a determination is made (at DECISION OPERATION 320) that the qualification data satisfies qualification criteria for an assistance program, at OPERATION 324, the method 300 uses the screening engine 160 to determine a discounted obligation amount corresponding to each assistance program for which the user qualifies. For example, the method 300 can use the screening engine 160 to apply a particular percentage discount or a particular dollar amount discount to an owed/obligation amount included in an ongoing transaction record 128 based on percentage or dollar discount data defined in the assistance program rules 116 associated with the assistance program for which the user qualifies. The method 300 may further use the screening engine 160 to rank the assistance programs according to the discounted obligation amounts.

At OPERATION 326, the method 300 uses the screening engine 160 to generate and communicate a response (4d) to the self-service portal 140 based on the results of the qualification determination. For example, the response (4d) can include information that indicates that the user qualifies for one or more assistance programs and the discounted obligation amount(s).

In response to the self-service portal 140 generating and displaying a UI 120 including an indication of the qualification determination(s), receiving a user selection (5a) to apply for/enroll in one or more of the application programs for which the user qualifies, and communicating those selections to the enrollment engine 170 (e.g., as part of an enrollment API request (5b)), at OPERATION 328, the method 300 uses the enrollment engine 170 to receive the user's selection(s) as a request to apply for/enroll in the selected assistance program(s).

At OPERATION 330, the method 300 uses the enrollment engine 170 to enroll the user in the selected assistance program(s) by communicating the user's enrollment selection(s) as part of an enrollment request (e.g., an API call or other communication medium) directed to one or more of the corresponding assistance program system(s) 132, the corresponding service provider system(s) 104, and/or the corresponding service provider system(s) via the patient access workflow system 190.

At DECISION OPERATION 332, the method 300 uses the enrollment engine 170 to determine whether additional user input (e.g., user signature, demographic data, financial data, health-related data) and/or particular supporting documents (e.g., bank statements, tax documents, income documents) may be needed to complete the enrollment process for an assistance program (e.g., according to assistance program rules 116 and/or service provider policies 118).

When a determination is made that additional user input and/or supporting documents are needed to complete the enrollment process for the user, the method 300 uses the enrollment engine 170 at OPERATION 334 to generate or select one or more supplementary questions 138 directed to the user based on the additional user-provided data needed for enrolling the user in one or more assistance programs, and to respond to the user's enrollment request (5b) with a response communicated to the self-service portal 140 including the one or more supplementary questions 138 associated with the needed user input data, a list of supporting documents (e.g., documents that serve as a proof of address, proof of income, proof of employment, proof of assets, proof of student status, proof of a medical condition or disability, proof of military service) required by the assistance program(s) and/or service provider(s), and an interface for uploading the supporting documents.

In response to the self-service portal 140 generating and displaying a UI 120 including the supplementary questions 138, the list of required supporting documents, and the interface for uploading the supporting documents, receiving user input/responses (6c) to the supplementary questions 138 and/or one or more supporting documents, and sending those user input/responses (6c) and/or supporting documents to the enrollment engine 170, the method 300 uses the screening engine 160 at OPERATION 338 to receive the user input/responses (6c) and/or supporting documents and to provide those user input/responses (6c) and/or supporting documents to one or a combination of: the corresponding assistance program system(s) 132, the corresponding service provider system(s) 104, and the corresponding service provider system(s) via the patient access workflow system 190. In example aspects, the service provider system(s) 104 and/or the assistance program system(s) 132 may update the user's ongoing transaction records 128 with the discounted obligation amounts, and these updated ongoing transaction records can be transmitted to the APQE system 130 and stored in the data store 165. The method 300 ends at OPERATION 398.

In one aspect, the determination of whether the user qualifies for an assistance program is made in near real-time after user submits inputs for the questionnaire. Therefore, the user does not have to wait for a long time to know whether he/she qualifies for an assistance program. In addition, the screening questionnaire does not require the user to provide any documents. Therefore, the user can respond to the questionnaire in a shortened amount of time. Further, aspects of the disclosure obviate a need to collect and transmit sensitive information and sensitive supporting documents, such as tax returns, bank statements, etc., before knowing the user's eligibility for an assistance program. This results in a reduction of an amount of information to be submitted, thereby reducing the complexity of applying for and enrolling in an assistance program. In addition, aspects of the disclosure accelerate the process for determining whether user qualifies for an assistance program by eliminating one or more manual review processes. For example, a reduced amount of information is provided to an administrator of the assistance program system 132 and/or the service provider system 104, and the administrator may only be required to review information submitted by users who have been determined to qualify for the assistance program (s). In addition, by first determining the user's qualification for an assistance program and collecting only the data relevant to assistance programs that the user qualifies for, the method 300 can reduce the amount of time to enroll in and receive the benefits of the assistance programs.

With reference now to FIG. 4A, a first example UI 120a is illustrated that includes a listing of a user's obligation amounts 402a-c (generally 402) associated with a plurality ongoing transaction records 128 for a plurality of service providers 404a-c (generally 404). For example, the first example UI 120a can be generated by the self-service portal 140 and displayed on a screen of the user computing device 102 for enabling the user to view the obligation amounts 402 and to check whether he/she qualifies to receive assistance with one or more of the obligation amounts 402. In example aspects, the first example UI 120a includes a selectable control 406 that enables the user to view additional information in association with one or more ongoing transaction records 128.

In example aspects, the first example UI 120a includes a plurality of selectors 408a-c (generally 408) for enabling the user to select which obligation amounts 402 for which the user is interested receiving assistance and an input control 410, which when selected, causes the self-service portal 140 to transmit a request to the APQE system 130 for determining one or more assistance programs for which the user may qualify to receive assistance. For example, the user can select a first selector 408a corresponding to a first obligation amount 404a and then select the input control 410 to initiate a qualification request (3b) for determining one or more assistance programs for which the user may qualify to receive assistance for the first obligation amount. Although the first example UI 120a is illustrated as displayed on a desktop computing device screen, in other examples, the first example UI 120a may be adapted for display on other form factor computing devices 102.

With reference now to FIG. 4B, a second example UI 120b is illustrated that includes a set of user-specific questions 138a-c for obtaining qualification data needed to make a determination regarding the user's qualification to receive assistance for one or more obligation amounts 404. For example, the second example UI 120b includes a display of the questionnaire 412 generated by the questionnaire generator 150 and includes questions 138a-c that the questionnaire generator selects or generates for receiving user responses that correlate with qualification data that may not be included in user data 126 and financial data 122 retrieved from one or more service provider systems 104 and one or more third-party data sources 106 respectively. In example aspects, the second example UI 120b includes one or more input controls 414a-c (respectively 414) that enable the user to input user responses to the one or more questions 138a-c. In example aspects, the second example UI 120b includes an input control 416 that enables the user to agree to certain terms or conditions. In example aspects, the second example UI 120b includes another input control 418, which when selected, transmits the user's responses to the APQE system 130 in a request for qualification results. In example aspects, the second example UI 120b includes another input control 420, which when selected, provides a display of one or more payment options. In example aspects, the second example UI 120b includes another input control 422, which when selected, provides a display of one or more assistance program applications. Although the second example UI 120b is illustrated as displayed on a mobile communication device screen, in other examples, the second example UI 120b may be adapted for display on other form factor computing devices 102.

FIGS. 4C and 4D are illustrations of a third example UI 120c. In one aspect, the UI 120c includes a display of a form 400 that the enrollment engine 170 transmits to the self-service portal 140 for obtaining additional user inputs, supporting documents, user signature, etc. In various examples, the form 400 corresponds to an application for a one or more assistance programs. In various examples, the form 400 can be completed in multiple steps with an ability to save with later retrieval features. With reference to FIG. 4C, the third example UI 120c includes a set of additional user-specific questions 424a-n for obtaining additional user inputs, a document upload interface 426 for obtaining documents needed to enroll the user in an assistance program, and a signature input interface 428 for obtaining the user's signature. For example, the set of additional user-specific questions 424a-n include a set of questions generated for the user for obtaining specific user inputs corresponding to specific application or enrollment criteria specified by a selected assistance program or service provider. In example aspects, information that is already known about the user (e.g., based on collect user data 126, financial data 122, user responses to questions 138), may be pre-filled in one or more input controls 425 included in the UI 120c.

In example aspects, the document upload interface 426 includes an input field to upload documents. For example, the document upload interface 426 can include an input field to drop files to upload. In example aspects, the user can drop files by taking pictures of the documents using an attached peripheral imaging device or using a drag and drop feature for an existing file. In example aspects, the document upload interface 426 can be used to upload multiple documents. In example aspects, documents that have been previously uploaded to the enrollment engine 170 via the self-service portal 140 can be listed in a previously uploaded documents section 428 of the third example UI 120c. In example aspects, the list of uploaded documents in the previously uploaded documents section 428 is automatically updated each time a new document is uploaded in document upload interface 426.

With reference now to FIG. 4D, in example aspects, the third example UI 120c includes a signature input field 430 that enables the user to input a signature. In example aspects, user can input the signature using a touch sensitive device or a digital signature. In example aspects, the third example UI 120c further includes an acknowledgement portion 432. In some examples, the form 400 can be enabled to be submitted to the enrollment engine 170 after acknowledgment fields 434a-c of the acknowledgement portion 432 are marked as complete. For example, the acknowledgement fields 434a-c may correspond to supporting documents specified by application or enrollment criteria. In example aspects, the third example UI 120c further includes a submit application control 436, which when selected, submits the form 400 to the enrollment engine 170. As should be appreciated, the example UIs 120a-c are not meant to be limiting, but are provided as examples. Other UI designs, functionalities, controls, interfaces, fields, and the like are possible and are within the scope of the present disclosure.

Figure 5:
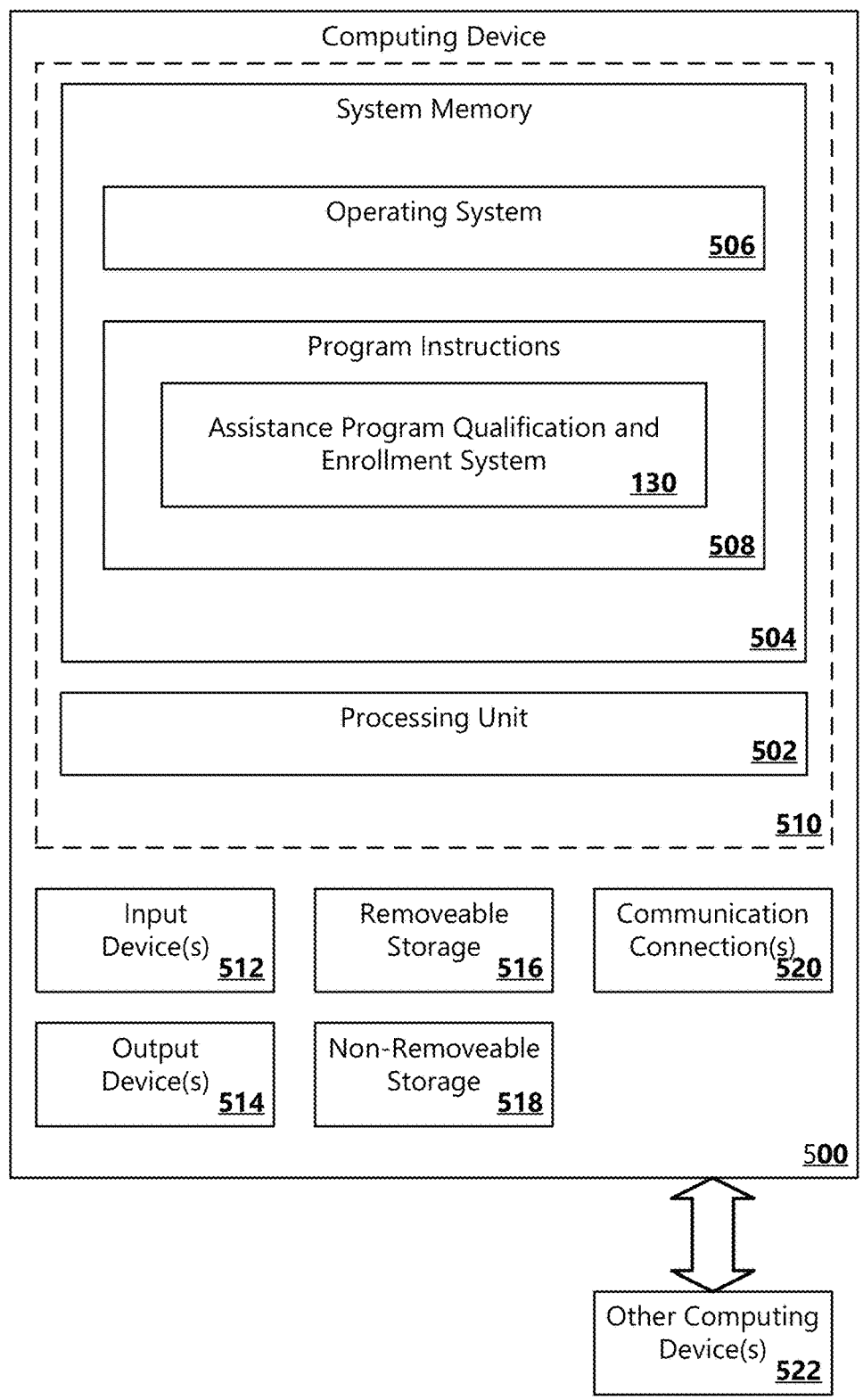
FIG. 5 is a block diagram illustrating example physical components of a computing device with which aspects of the system may be practiced.

FIG. 5 is a block diagram illustrating physical components of an example computing device with which aspects may be practiced. Computing device 500 may include at least one processing unit 502 and a system memory 504. System memory 504 may include, but is not limited to, volatile (e.g. random access memory (RAM)), non-volatile (e.g. read-only memory (ROM)), flash memory, or any combination thereof. System memory 504 may include an operating system 506, one or more program instructions 508, and may include sufficient computer-executable instructions for the APQE system 130, which when executed, perform automated assistance program qualification and enrollment functionalities as described herein. Operating system 506, for example, may be suitable for controlling the operation of computing device 500. Furthermore, aspects may be practiced in conjunction with a graphics library, other operating systems, or any other application program and is not limited to any particular application or system. This basic configuration is illustrated by those components within a dashed line 510. Computing device 500 may also include one or more input device(s) 512 (keyboard, mouse, pen, touch input device, etc.) and one or more output device(s) 514 (e.g., display, speakers, a printer, etc.).

Computing device 500 may also include additional data storage devices (removable or non-removable) such as, for example, magnetic disks, optical disks, or tape. Such additional storage is illustrated by a removable storage 516 and a non-removable storage 518. Computing device 500 may also contain a communication connection 520 that may allow computing device 500 to communicate with other computing devices 522, such as over a network in a distributed computing environment, for example, an intranet or the Internet. Communication connection 520 is one example of a communication medium, via which computer-readable transmission media (i.e., signals) may be propagated.

Programming modules may include routines, programs, components, data structures, and other types of structures that may perform particular tasks or that may implement particular abstract data types. Moreover, aspects may be practiced with other computer system configurations, including hand-held devices, multiprocessor systems, microprocessor-based or programmable user electronics, minicomputers, mainframe computers, and the like. Aspects may also be practiced in distributed computing environments where tasks are performed by remote processing devices that are linked through a communications network. In a distributed computing environment, programming modules may be located in both local and remote memory storage devices.

Furthermore, aspects may be practiced in an electrical circuit including discrete electronic elements, packaged or integrated electronic chips containing logic gates, a circuit using a microprocessor, or on a single chip containing electronic elements or microprocessors (e.g., a system-on-a-chip (SoC)). Aspects may also be practiced using other technologies capable of performing logical operations such as, for example, AND, OR, and NOT, including, but not limited to, mechanical, optical, fluidic, and quantum technologies. In addition, aspects may be practiced within a general purpose computer or in any other circuits or systems.

Aspects may be implemented as a computer process (method), a computing system, or as an article of manufacture, such as a computer program product or computer-readable storage medium. The computer program product may be a computer storage medium readable by a computer system and encoding a computer program of instructions for executing a computer process. Accordingly, hardware or software (including firmware, resident software, microcode, etc.) may provide aspects discussed herein. Aspects may take the form of a computer program product on a computer-usable or computer-readable storage medium having computer-usable or computer-readable program code embodied in the medium for use by, or in connection with, an instruction execution system.

Although aspects have been described as being associated with data stored in memory and other storage mediums, data can also be stored on or read from other types of computer-readable media, such as secondary storage devices, like hard disks, floppy disks, or a CD-ROM, or other forms of RAM or ROM. The term computer-readable storage medium refers only to devices and articles of manufacture that store data or computer-executable instructions readable by a computing device. The term computer-readable storage media do not include computer-readable transmission media.

Aspects of the present invention may be used in various distributed computing environments where tasks are performed by remote processing devices that are linked through a communications network.

Aspects of the invention may be implemented via local and remote computing and data storage systems. Such memory storage and processing units may be implemented in a computing device. Any suitable combination of hardware, software, or firmware may be used to implement the memory storage and processing unit. For example, the memory storage and processing unit may be implemented with computing device 500 or any other computing devices 522, in combination with computing device 500, wherein functionality may be brought together over a network in a distributed computing environment, for example, an intranet or the Internet, to perform the functions as described herein. The systems, devices, and processors described herein are provided as examples; however, other systems, devices, and processors may comprise the aforementioned memory storage and processing unit, consistent with the described aspects.

The description and illustration of one or more aspects provided in this application are intended to provide a thorough and complete disclosure the full scope of the subject matter to those skilled in the art and are not intended to limit or restrict the scope of the invention as claimed in any way. The aspects, examples, and details provided in this application are considered sufficient to convey possession and enable those skilled in the art to practice the best mode of the claimed invention. Descriptions of structures, resources, operations, and acts considered well-known to those skilled in the art may be brief or omitted to avoid obscuring lesser known or unique aspects of the subject matter of this application. The claimed invention should not be construed as being limited to any embodiment, aspects, example, or detail provided in this application unless expressly stated herein. Regardless of whether shown or described collectively or separately, the various features (both structural and methodological) are intended to be selectively included or omitted to produce an embodiment with a particular set of features. Further, any or all of the functions and acts shown or described may be performed in any order or concurrently. Having been provided with the description and illustration of the present application, one skilled in the art may envision variations, modifications, and alternate embodiments falling within the spirit of the broader aspects of the general inventive concept provided in this application that do not depart from the broader scope of the present disclosure.

We claim:

1. A system for providing automated assistance program qualification and enrollment, the system comprising:
   at least one processor; and
   a memory storage device including instructions that when executed by the at least one processor are configured to:
     provide a questionnaire generator, the questionnaire generator configured to:
       receive a request for a determination of a user's qualification for an assistance program for receiving assistance in association with an ongoing transaction record;
       evaluate assistance program rules and a service provider policy corresponding to the ongoing transaction record for determining qualification data that are evaluated as part of determining the user's qualification for one or more assistance programs;
       retrieve user data that include information about the user collected by one or more service providers, wherein:
         the one or more service providers include the service provider corresponding to the ongoing transaction record; and
         the user data include qualification data for the one or more assistance programs;
       retrieve financial data about the user from a third-party data source, wherein the financial data include qualification data for the one or more assistance programs;
       determine which qualification data are not included in the retrieved user data and financial data;
       generate a questionnaire comprising one or more questions, wherein the one or more questions correlate with the qualification data not included in the retrieved user data and financial data;
       transmit the questionnaire to a self-service portal configured to:
         generate a user interface for display to the user, wherein the user interface includes the questionnaire;
         receive user responses to the questionnaire via the user interface; and
         transmit the user responses to a screening engine;

provide a screening engine, the screening engine configured to:
  receive the user responses;
  evaluate the user responses, the user data, and the financial data for determining whether the user responses, user data, and financial data satisfy qualification criteria for an assistance program of the one or more assistance programs;
  when the qualification criteria for a first assistance program are satisfied:
    determine a discounted obligation amount for the ongoing transaction record based on the first assistance program;
    include, in a response, an indication that the user is qualified to receive assistance provided by the first assistance program and the discounted obligation amount; and
    transmit the response to the self-service portal for display to the user in the user interface; and
provide an enrollment engine, the enrollment engine configured to:
  receive, via the self-service portal, a user request to enroll in the first assistance program; and
  enroll the user in the first assistance program,
identify, via the screening engine, a second assistance program of the one or more assistance programs based at least in part on the user request to enroll in the first assistance program and the assistance program rules;
determine, via the screening engine, that an enrollment of the user in the second assistance program conflicts with the enrollment of the user in the first assistance program; and
disable, via the screening engine, input controls in the self-service portal for the user for selecting and enrolling in the second assistance program.

2. The system of claim 1, wherein when the qualification criteria for a plurality of assistance programs are satisfied, the screening engine is further configured to:
  determine a plurality of discounted obligation amounts for the ongoing transaction record based on the plurality of assistance programs;
  include, in the response, a list of assistance programs for which the user is qualified to receive assistance, the list including the plurality of assistance programs ranked according to the discounted obligation amounts; and
  transmit the response to the self-service portal for display to the user in the user interface.

3. The system of claim 2, wherein:
  in receiving the request for a determination of the user's qualification for an assistance program, the questionnaire generator is configured to receive a request for a determination of the user's qualification for an assistance program for receiving assistance in association with a plurality of ongoing transaction records;
  in evaluating the assistance program rules and the service provider policy corresponding to the ongoing transaction record, the questionnaire generator is configured to evaluate the assistance program rules and the service provider policy corresponding to each of the plurality of ongoing transaction records; and
  in retrieving user data that include information about the user collected by one or more service providers, the questionnaire generator is configured to retrieve user data that include information about the user collected by each of the service providers associated with an ongoing transaction record of the plurality of transaction records.

4. The system of claim 3, wherein:
  in determining the plurality of discounted obligation amounts for the ongoing transaction record based on the plurality of assistance programs, the screening engine is configured to determine a plurality of discounted obligation amounts for each of the plurality of ongoing transaction records based on the plurality of assistance programs;
  in including, in the response, the list of assistance programs for which the user is qualified to receive assistance, the screening engine is configured to include a list for each ongoing transaction record, wherein:
    each list for each ongoing transaction record includes a ranked list of the plurality of assistance programs for which the user is qualified to receive assistance; and
    the ranked list is ranked according to the discounted obligation amounts; and
  in receiving the user request to enroll in the first assistance program, the enrollment engine is configured to receive:
    a user request to enroll in the first assistance program for receiving assistance in association with a first ongoing transaction record; and
    a user request to enroll in a third assistance program for receiving assistance in association with a third ongoing transaction record; and
  in enrolling the user in the first assistance program, the enrollment engine is configured to:
    enroll the user in the first assistance program for receiving assistance in association with the first ongoing transaction record; and
    enroll the user in the third assistance program for receiving assistance in association with the third ongoing transaction record.

5. The system of claim 4, wherein in including, in the response, the list for each ongoing transaction record, the screening engine is configured to include instructions in the response that enable the self-service portal to prevent user requests for conflicting enrollments in more than one assistance program.

6. The system of claim 5, wherein the assistance program rules and the service provider policies corresponding to each of the plurality of ongoing transaction records define the conflicting enrollments.

7. The system of claim 1, wherein responsive to receiving the user request to enroll in the first assistance program, the enrollment engine is further configured to:
  determine whether additional user input and supporting documents are required as part of completing an enrollment process for the user in the first assistance program; and
  when a determination is made that additional user input and supporting documents are required as part of completing the enrollment process:
  generate or select one or more supplementary questions directed to the user based on the additional user data required as part of completing the enrollment process; and
  transmit, to the self-service portal, the one or more supplementary questions in a response to the user request, wherein the response further includes a list of the supporting documents required as part of completing the enrollment process and instructions for enabling the self-service portal to generate a user interface including an interface for uploading and transmitting the supporting documents to the enrollment engine.

8. The system of claim 7, wherein the one or more supplementary questions directed to the user correspond to an application for the first assistance program.

9. The system of claim 7, wherein:
the additional user data required as part of completing the enrollment process in the first assistance program include one or more of:
a user signature;
demographic data about the user; financial data about the user; and health- related data about the user; and
the supporting documents required as part of completing the enrollment process in the first assistance program include documents that provide proof of one or more of:
residency;
income;
employment or non-employment;
assets;
student status;
a medical condition;
disability; and
military service.

10. A method for providing automated assistance program qualification and enrollment, comprising:
using a questionnaire generator as part of:
receiving a request for a determination of a user's qualification for an assistance program for receiving assistance in association with an ongoing transaction record;
evaluating assistance program rules and a service provider policy corresponding to the ongoing transaction record for determining qualification data that are evaluated as part of determining the user's qualification for one or more assistance programs;
retrieving user data that include information about the user collected by one or more service providers, wherein:
the one or more service providers include the service provider corresponding to the ongoing transaction record; and
the user data include qualification data for the one or more assistance programs;
retrieving financial data about the user from a third-party data source, wherein the financial data include qualification data for the one or more assistance programs;
determining which qualification data are not included in the retrieved user data and financial data;
generating a questionnaire comprising one or more questions, wherein the one or more questions correlate with the qualification data not included in the retrieved user data and financial data; and
transmitting the questionnaire to a self-service portal configured to:
generate a user interface for display to the user, wherein the user interface includes the questionnaire;
receive user responses to the questionnaire via the user interface; and
transmit the user responses to a screening engine;
using a screening engine as part of:
receiving the user responses;
evaluating the user responses, user data, and financial data for determining whether the user responses, user data, and financial data satisfy qualification criteria for an assistance program of the one or more assistance programs; and
when the qualification criteria for a first assistance program are satisfied:
determining a discounted obligation amount for the ongoing transaction record based on the first assistance program;
including, in a response, an indication that the user is qualified to receive assistance provided by the first assistance program and the discounted obligation amount; and
transmitting the response to the self-service portal for display to the user in the user interface;
using an enrollment engine as part of:
receiving, via the self-service portal, a user request to enroll in the first assistance program; and
enrolling the user in the first assistance program; and
after enrolling the user in the first assistance program, via the screening engine:
identifying a second assistance program of the one or more assistance programs based at least in part on the user request to enroll in the first assistance program and the assistance program rules;
determining that an enrollment of the user in the second assistance program conflicts with the enrollment of the user in the first assistance program; and
disabling input controls in the self-service portal for the user for selecting and enrolling in the second assistance program.

11. The method of claim 10, further comprising:
when the qualification criteria for a plurality of assistance programs are determined to be satisfied:
determining a plurality of discounted obligation amounts for the ongoing transaction record based on the plurality of assistance programs;
including, in the response, a list of assistance programs for which the user is qualified to receive assistance, the list including the plurality of assistance programs ranked according to the discounted obligation amounts; and
transmitting the response to the self-service portal for display to the user in the user interface.

12. The method of claim 11, wherein:
receiving the request for a determination of the user's qualification for an assistance program comprises receiving a request for a determination of the user's qualification for an assistance program for receiving assistance in association with a plurality of ongoing transaction records;
evaluating the assistance program rules and the service provider policy corresponding to the ongoing transaction record comprises evaluating the assistance program rules and the service provider policy corresponding to each of the plurality of ongoing transaction records; and
retrieving user data that include information about the user collected by one or more service providers comprises retrieving user data that include information about the user collected by each of the service providers associated with an ongoing transaction record of the plurality of transaction records.

13. The method of claim 12, wherein:
determining the plurality of discounted obligation amounts for the ongoing transaction record based on the plurality of assistance programs comprises determining a plurality of discounted obligation amounts for each of the plurality of ongoing transaction records based on the plurality of assistance programs;
including, in the response, the list of assistance programs for which the user is qualified to receive assistance comprises including a list for each ongoing transaction record, wherein:
each list for each ongoing transaction record includes a ranked list of the plurality of assistance programs for which the user is qualified to receive assistance; and
the ranked list is ranked according to the discounted obligation amounts; and
receiving the user request to enroll in the first assistance program comprises receiving:
a user request to enroll in the first assistance program for receiving assistance in association with a first ongoing transaction record; and
a user request to enroll in a third assistance program for receiving assistance in association with a third ongoing transaction record; and enrolling the user in the first assistance program comprises:
enrolling the user in the first assistance program for receiving assistance in association with the first ongoing transaction record; and
enrolling the user in the third assistance program for receiving assistance in association with the third ongoing transaction record.

14. The method of claim 13, wherein including, in the response, the list for each ongoing transaction record comprises including instructions in the response that enable the self-service portal to prevent user requests for conflicting enrollments in more than one assistance program, wherein the conflicting enrollments are defined by the assistance program rules and the service provider policies corresponding to each of the plurality of ongoing transaction records.

15. The method of claim 10, wherein responsive to receiving the user request to enroll in the first assistance program, further comprising:
determining whether additional user input and supporting documents are required as part of completing an enrollment process for the user in the first assistance program; and
when a determination is made that additional user input and supporting documents are required as part of completing the enrollment process:
generating or selecting one or more supplementary questions directed to the user based on the additional user data required as part of completing the enrollment process; and
transmitting, to the self-service portal, the one or more supplementary questions in a response to the user request, wherein the response further includes a list of the supporting documents required as part of completing the enrollment process and instructions for enabling the self-service portal to generate a user interface including an interface for uploading and transmitting the supporting documents to the enrollment engine.

16. The method of claim 15, wherein:
generating or selecting one or more supplementary questions directed to the user comprises selecting an application form for the first assistance program; and
transmitting, to the self-service portal, the one or more supplementary questions in a response to the user request comprises transmitting the application form to the self-service portal.

17. The method of claim 15, wherein prior to transmitting the application form, pre-filling one or more fields of the form with information in the retrieved user data and financial data and previously-received user responses.

18. A computer readable storage device including computer readable instructions, which when executed by a processing unit are configured to:
provide a questionnaire generator, the questionnaire generator configured to:
receive a request for a determination of a user's qualification for an assistance program for receiving assistance in association with one or more ongoing transaction records;
evaluate assistance program rules and a service provider policy corresponding to each of the one or more ongoing transaction records for determining qualification data that are evaluated as part of determining the user's qualification for one or more assistance programs;
retrieve user data that include information about the user collected by one or more service providers, wherein:
the one or more service providers include the service providers corresponding to the one or more ongoing transaction records; and
the user data include qualification data for the one or more assistance programs;
retrieve financial data about the user from a third-party data source, wherein the financial data include qualification data for the one or more assistance programs;
determine which qualification data are not included in the retrieved user data and financial data;
generate a questionnaire comprising one or more questions, wherein the one or more questions correlate with the qualification data not included in the retrieved user data and financial data; and
transmit the questionnaire to a self-service portal configured to:
generate a user interface for display to the user, wherein the user interface includes the questionnaire;
receive user responses to the questionnaire via the user interface; and
transmit the user responses to a screening engine;
provide a screening engine, the screening engine configured to:
receive the user responses;
evaluate the user responses, user data, and financial data for determining whether the user responses, user data, and financial data satisfy qualification criteria for an assistance program of the one or more assistance programs;
after the qualification criteria for a first assistance program is satisfied:
determine a discounted obligation amount for the ongoing transaction record based on the first assistance program;
include, in a response, an indication that the user is qualified to receive assistance provided by the first assistance program and the discounted obligation amount; and
transmit the response to the self-service portal for display to the user in the user interface; and
provide an enrollment engine, the enrollment engine configured to:
receive, via the self-service portal, a user request to enroll in the first assistance program; and
enroll the user in the first assistance program, identify, via the screening engine, a second assistance program of the one or more assistance programs based at least in part on the user request to enroll in the first assistance program and the assistance program rules;

determine, via the screening engine, that an enrollment of the user in the second assistance program conflicts with the enrollment of the user in the first assistance program; and disable, via the screening engine, input controls in the self-service portal for the user for selecting and enrolling in the second assistance program.

19. The computer readable storage device of claim 18, wherein:

in transmitting the response to the self-service portal for display to the user in the user interface further includes transmitting instructions in the response that enable the self-service portal to prevent user requests for conflicting enrollments in more than one assistance program; and the conflicting enrollments are defined in the assistance program rules and the service provider policies corresponding to each of the plurality of ongoing transaction records.

20. The computer readable storage device of claim 18, wherein responsive to receiving the user request to enroll in one or more assistance programs, the enrollment engine is further configured to:

determine whether additional user input and supporting documents are required as part of completing enrollment processes for the user in the one or more assistance programs; and when a determination is made that additional user input and supporting documents are required as part of completing the enrollment processes:

generate or select one or more supplementary questions directed to the user based on the additional user data required as part of completing the enrollment processes; and transmit, to the self-service portal, the one or more supplementary questions in a response to the user request, wherein the response further includes a list of the supporting documents required as part of completing the enrollment processes and instructions for enabling the self-service portal to generate a user interface including an interface for uploading and transmitting the supporting documents to the enrollment engine.

* * * * *